United States Patent
De Craene et al.

(10) Patent No.: US 11,713,488 B2
(45) Date of Patent: Aug. 1, 2023

(54) BIOMARKER PANEL AND METHODS FOR DETECTING MICROSATELLITE INSTABILITY IN CANCERS

(71) Applicant: Biocartis NV, Mechelen (BE)

(72) Inventors: Bram De Craene, Mechelen (BE); Klaas Decanniere, Mechelen (BE); Jan Van De Velde, Mechelen (BE); Geert Maertens, Mechelen (BE)

(73) Assignee: BIOCARTIS NV, Mechelen (BE)

( * ) Notice: Subject to any disclaimer, the term of this patent is extended or adjusted under 35 U.S.C. 154(b) by 0 days.

(21) Appl. No.: 16/767,968

(22) PCT Filed: Jan. 22, 2019

(86) PCT No.: PCT/EP2019/051515
§ 371 (c)(1),
(2) Date: May 28, 2020

(87) PCT Pub. No.: WO2019/145306
PCT Pub. Date: Aug. 1, 2019

(65) Prior Publication Data
US 2020/0399705 A1    Dec. 24, 2020

(30) Foreign Application Priority Data

Jan. 23, 2018 (EP) .................................... 18153056
Apr. 19, 2018 (EP) .................................... 18168304

(51) Int. Cl.
*C12Q 1/6886* (2018.01)
(52) U.S. Cl.
CPC ..... *C12Q 1/6886* (2013.01); *C12Q 2600/156* (2013.01)
(58) Field of Classification Search
None
See application file for complete search history.

(56) References Cited

FOREIGN PATENT DOCUMENTS

| EP | 1896180 | 3/2008 |
| EP | 1904234 | 4/2008 |
| EP | 2419705 | 2/2012 |
| WO | 2006047412 | 5/2006 |
| WO | 2007004103 | 1/2007 |
| WO | 2013153130 | 10/2013 |
| WO | WO 2013/153130 | * 10/2013 |
| WO | WO 2017/050934 | * 3/2017 |

OTHER PUBLICATIONS

Bonneville (JCO Precision Oncology 2017 :1, 1-15).*
Cortes-Ciriano (Nature Communications 8:15180 pub Jun. 6, 2017).*
Boland, C. R., et al. "A National Cancer Institute Workshop on Microsatellite Instability for cancer detection and familial predisposition: development of international criteria for the determination of microsatellite instability in colorectal cancer." (1998): 5248-5257.
Buhard, O., et al. "Multipopulation analysis of polymorphisms in five mononucleotide repeats used to determine the microsatellite instability status of human tumors." Journal of clinical oncology 24.2 (2006): 241-251.
Campbell, B. B., et al. "Comprehensive analysis of hypermutation in human cancer." Cell 171.5 (2017): 1042-1056.
De Craene, B. et al. "Detection of microsatellite instability (MSI) with a novel panel of biomarkers in gastric cancer samples", Sep. 12, 2017. Retrieved from the Internet: URL:http://biocartis.com/sites/default/files/2018-10/de_craene_b._et_al_idylla_msi_in_gastric_samples._esmo_2017_poster_697p.pdf.
Ellegren, H. "Microsatellites: simple sequences with complex evolution." Nature reviews genetics 5.6 (2004): 435-445.
Endris, V. et al. Detection of microsatellite instable colorectal cancers from routine NGS panel sequencing data [abstract]. In: Proceedings of the American Association for Cancer Research Annual Meeting 2017; Apr. 1-5, 2017; Washington, DC. Philadelphia (PA): AACR; Cancer Res 2017;77(13 Suppl):Abstract nr 3735.
International Searching Authority. International Search Report and Written Opinion for application PCT/EP2019/051515, dated Feb. 25, 2019.
Le, D. T., et al. "PD-1 blockade in tumors with mismatch-repair deficiency." New England Journal of Medicine 372.26 (2015): 2509-2520.
Llosa, N. J., et al. "The vigorous immune microenvironment of microsatellite instable colon cancer is balanced by multiple counter-inhibitory checkpoints." Cancer discovery 5.1 (2015): 43-51.
Maruvka, Y. E., et al. "Analysis of somatic microsatellite indels identifies driver events in human tumors." Nature biotechnology 35.10 (2017): 951.
Murphy, K. M., et al. "Comparison of the microsatellite instability analysis system and the Bethesda panel for the determination of microsatellite instability in colorectal cancers." The Journal of Molecular Diagnostics 8.3 (2006): 305-311.
Turajlic, S., et al. "Insertion-and-deletion-derived tumour-specific neoantigens and the immunogenic phenotype: a pan-cancer analysis." The lancet oncology 18.8 (2017): 1009-1021.
Webber, E. M., et al. "Systematic review of the predictive effect of MSI status in colorectal cancer patients undergoing 5FU-based chemotherapy." BMC cancer 15.1 (2015): 156.
Zhao, H., et al. "Mismatch repair deficiency endows tumors with a unique mutation signature and sensitivity to DNA Jouble-strand breaks." Elife 3 (2014): e02725.

* cited by examiner

*Primary Examiner* — Amanda Haney
(74) *Attorney, Agent, or Firm* — Quarles & Brady LLP

(57) ABSTRACT

The present invention generally relates to the field of cancer, in particular to cancers having microsatellite instability (MSI) and/or mismatch repair (MMR-) deficiency. Examples of such cancers include many colorectal, gastric, and endometrial tumors. Accordingly, the present invention provides a novel diagnostic marker panel for analyzing MSI loci, together with methods and kits of using said panel in the detection of cancers having microsatellite instability (MSI) and/or mismatch repair (MMR-) deficiency.

9 Claims, 6 Drawing Sheets

Specification includes a Sequence Listing.

| Stage | Idylla™ MSI Test | | | | | IHC | | | | Discordant Idylla™ MSI Test versus IHC |
|---|---|---|---|---|---|---|---|---|---|---|
| | MS-H | MSS | total Valid | Invalid | Error | MS-H | MSS | total Valid | Failed | |
| unknown | 5 | 9 | 14 | 2 | 0 | 6 | 9 | 15 | 1 | 2 |
| I | 2 | 20 | 22 | 0 | 0 | 2 | 19 | 21 | 1 | 0 |
| II | 16 | 48 | 64 | 0 | 0 | 17 | 44 | 61 | 3 | 1 |
| III | 33 | 110 | 143 | 0 | 0 | 33 | 106 | 139 | 4 | 2 |
| IV | 19 | 66 | 85 | 0 | 0 | 22 | 62 | 84 | 1 | 3 |
| Total | 75 | 253 | 328 | 2 | 0 | 80 | 240 | 320 | 10 | 8 |
| Overall total | | | 330 | | | | | 330 | | 8 |

BIOMARKER PANEL AND METHODS FOR DETECTING MICROSATELLITE INSTABILITY IN CANCERS

CROSS-REFERENCED TO RELATED PATENT APPLICATIONS

This application is a U.S. National Stage of International Application No. PCT/EP2019/051515 filed on Jan. 22, 2019, which claims the benefit of European Patent Application No. 18153056.9, filed on Jan. 23, 2018 and European Patent Application No. 18168304.6, filed on Apr. 19, 2018, the contents of which are incorporated herein by reference in their entireties.

SEQUENCE LISTING

This application is filed electronically via EFS-Web and includes an electronically submitted Sequence Listing in .txt format. The txt file contains a sequence listing entitled "00023seqltg.txt" created on May 28, 2020 and is 3,515 bytes in size. The Sequence Listing contained in this .txt file is part of the specification and is hereby incorporated by reference herein in its entirety.

TECHNICAL FIELD

The present invention generally relates to the field of cancer, in particular to cancers having microsatellite instability (MSI) and/or mismatch repair (MMR-) deficiency. Examples of such cancers include many colorectal, gastric, and endometrial tumors. Accordingly, the present invention provides a novel diagnostic marker panel for analyzing MSI loci, together with methods and kits of using said panel in the detection of cancers having microsatellite instability (MSI) and/or mismatch repair (MMR-) deficiency.

BACKGROUND OF THE INVENTION

Each year in Europe and USA approximately 440,000 patients are diagnosed with colorectal cancer (CRC). Recent guidelines, such as NCCN Guidelines for Patients: Colon Cancer Version 1.2017, and ESMO Clinical Practice Guidelines on familial risk-colorectal cancer recommend tumor testing for DNA mismatch repair (MMR) deficiently and/or MSI status in all CRC patients. Yet, today these tests are still vastly underused due to their underlying technical complexity. In particular, it is difficult to test for all the possible mutations underlying MMR deficiency and although there exist alternative approaches to screen it, the present assays still require extensive manipulation time in the laboratory and therefore are not fit to become diagnostic routine.

The above obstacles naturally affect management and thus potentially also survival rates of many cancer patients. Indeed, in a substantial subset of colorectal carcinoma (CRC) cases, deficiencies in MMR genes are found to be pivotal for tumorigenesis and disease progression. For example, epigenetic silencing of the MMR gene MLH1 accounts for around 12% of CRC. A further 2-5% of cases are caused by an autosomal dominantly inherited loss-of-function mutations in one of the MMR genes MLH1, MSH2, PMS2 or MSH6. This familial cancer susceptibility disorder is known as the Lynch syndrome or hereditary non-polyposis CRC (HNPCC) and further leads to an increased risk for also gastric and endometrial carcinoma (amongst others).

The MMR pathway involves a great deal of genes and many diverse genetic and epigenetic lesions were identified to affect it. Several others likely remain to be still identified. Therefore, it is more practical to diagnose deficiencies in the MMR machinery through screening for their direct result. The latter being a genome-wide accumulation of DNA replication errors which can be observed as changes in nucleotide number due to deletion or insertion within single and di-nucleotide repeat sequences, for example $(A)_n$ or $(CA)_n$. This phenomenon is known as microsatellite instability or MSI. When MMR deficiency leads to MSI in coding regions it most frequently results in promoter or frameshift mutations leading to lack of expression, expression of truncated proteins, and/or proteins containing extensive novel sequences containing neoantigens. Furthermore, MSI in intron-exon boundary regions were shown to affect RNA splicing mechanisms and therefore also interfere with protein translation. Overall, MSI phenotype correlates with genomic instability, higher mutation rate, and consequently in different tumor behavior and prognosis.

MSI-high (MSI-H) tumors in general have better prognosis and reduced likelihood of metastasis compared with microsatellite stable (MSS) tumors. Moreover, these two tumor types also react differently to different treatments. For example, early MSI CRCs generally do not respond to 5-fluorouracil-based chemotherapy, currently being the golden standard in CRC treatment (e.g. Webber et al., 2015). On the other hand, MSI tumors exhibit increased levels of at least five immune checkpoint molecules that are targets for therapeutic inhibitors currently being clinically tested (Llosa et al. 2014). For example, colorectal cancer patients with mismatch repair deficiency are expected to respond particularly well to anti-PD-1 immunotherapy, which acts by blocking the interaction between PD-1 receptors on T-cells and PD-L1 and PD-L2 receptors on tumor cells, disabling their immune system avoidance mechanisms (Le et al., 2015). Multiple other compounds and bioactive substances, such as camptothecin or irinotecan, are currently also being tested for targeted tumor therapies based on the unique molecular footprint of MSI.

Thus, it is already recognized that MSI status identification in tumors may have a huge impact on the treatment outcome and consequently also on the quality of life and a life expectancy of many cancer patients. This is best demonstrated by the fact that many official guidelines already openly recommend MSI testing in colon cancer and Lynch syndrome. They include e.g. NCCN Guidelines for Colon Cancer, ESMO Clinical practice Guidelines on familial risk-colorectal cancer, Revised Bethesda Guidelines, Amsterdam II clinical criteria, US Multisociety Task Force on Colorectal Cancer etc.

Currently, two techniques are most often used for MSI testing; immunohistochemistry (IHC) and capillary electrophoresis. IHC is an expensive, labor-intensive, and time-consuming technique with a high rate of false negative results. In capillary electrophoresis, fluorescent PCR is used to amplify specific genomic regions containing nucleotide repeats in tumor cells and normal cells, after which the presence of the instability is determined by comparing the length of the amplification products. There exist hundreds of thousands of microsatellite loci throughout the genome that can potentially be used in MSI analysis (Ellegren, *Nat Rev Genet.* 2004).

For example, the consensus MSI panel established in 1997 and known as the Bethesda panel includes 5 microsatellite markers including 2 mono- or homonucleotide repeats of 25 and 26 nucleotides in length (BAT25 and BAT26, respectively), and 3 dinucleotide repeats (D2S123, D5S346, D17S250) (Boland et al, 1998). A sample tested with the Bethesda panel is designated as having a high-frequency of MSI or an "MSI-H" phenotype if 30% or more of the markers (so at least 2 in the 5-marker panel) were tested as unstable. If one marker out of five (or <30% of tumor markers) scores as MSI positive, a sample is designated as MSI-low or "MSI-L". Finally, if no marker is found altered, a sample is considered MSI-stable or "MSS" (Boland et al, 1998).

However, despite being the current MSI testing standard, the Bethesda panel suffers from several drawbacks such as unequal prevalence of the loci in different ethnical populations and different tumor types. Especially, it tends to show low sensitivity, especially in cancers other than colorectal cancer in view of which it was initially developed (Boland et al, 1998). These and other factors have led to its expansion and/or diversification with additional markers by individual clinicians and research laboratories, which has consequently resulted in loss of standardization and poor reproducibility. Examples of the above include e.g. Murphy et al, 2006 and WO2006047412 (Promega). Alternatively, completely new microsatellite markers that do not overlap with any of the Bethesda panel were also described, e.g. in WO2013153130 (VIB) and Zhao et al, 2014 (eLife).

Another drawback of the currently known approaches is their level of complication, need of specialized instruments extending beyond the standard laboratory thermocyclers, as well as their limited feasibility for automation. The classical Bethesda panel testing itself is an open-tube test, which increases the chance of cross-contamination. Furthermore, it requires specialized lab personnel and is time-consuming, expensive, and labor-intensive. Generally, the currently existing detection techniques of MSI apply one of the following principles: (i) use of fluorescently labelled primers for detection of the Bethesda panel markers, followed by capillary electrophoresis; (ii) high-resolution melting curve analysis of the 5 Bethesda panel markers using a dsDNA-intercalating dye; (iii) mass spectrometric detection of alleles of a different length; and (iv) next-generation sequencing (NGS) of large DNA regions (e.g. exome) followed by counting the number of mutations, or of a number of homopolymer regions in a non-matched setup (Campbell et al., 2017, Cell).

In (i), for example, the initial PCR-based Bethesda screening strategy requires an expert observer's interpretation that hinders effective and straightforward automation. Then, concerning (ii), the high-resolution melting curve analysis with dsDNA-intercalating dyes suffers from very limited multiplexing abilities for screening several different MSI markers in one run since the melting temperature for each marker amplicon needs to be sufficiently different in order not to produce overlapping signals. Furthermore, as this strategy relies on formation of heteroduplexes between normal and mutant length alleles, it is also less sensitive as compared to the other alternatives. Next, concerning (iii), the mass spectrometry-based method (Zhao et al, 2014) is in principle also amenable to automation but requires specialized instrumentation and highly skilled personnel for the data interpretation. Lastly, with regard to (iv), while NGS undoubtedly has the advantage of looking at a very large number of MSI-indicative positions in the genome or exome rather than only at the selective markers and although this method is also in principle at least partially automatable, it is currently very expensive and requires specialized NGS hardware. With regard to homopolymer scoring, NGS is still not sufficiently robust to repeatedly score individual homopolymeric repeats as it is still prone to lose information about single nucleotide indels in a string of repeating nucleotides. In addition, due to generation of a large amounts of data, it remains time-consuming, complicated, and requires a highly trained analyst.

In conclusion, MSI testing represents a very high medical need that currently is only partially met by existing diagnostic methods due to their technical constraints. These importantly include limited detection capabilities, high costs and/or turnaround time, requirement of specialized equipment, and/or highly-trained expert's interpretation. The present invention solves the above-listed drawbacks by providing a highly sensitive set of only few short homopolymeric MSI markers of the kind as described in WO2013153130, together with an extremely robust method for detecting homonucleotide insertions or deletions (indels) within their sequences. This method is very automation-friendly, does not require specific molecular infrastructures and can be performed using standard laboratory equipment such as a simple thermocycler connected to a computer. In addition, it allows for easy duplexing or even higher-level multiplexing of the selected markers, which confers the advantage of even further limiting the required laboratory material and thus facilitating implementation onto existing PCR-based platforms. Importantly, the method provides very consistent results and allows an easy and fully automatic interpretation with a direct report as an output. In current settings, from receiving a patient's tissue sample, we show that we can obtain such full read-outs of the indels' statuses within less than 3 hours. Thus, the presented herein novel marker panel and method of its detection provide a new highly advantageous alternative for detecting MSI in CRC, even in its early stages (as we show below), and in other cancer samples, such as ovarian, endometrial, and gastric cancer, as well as for predictive and follow-up studies in the context of immunotherapy. These and other advantages and uses of the present invention are presented in continuation.

SUMMARY OF THE INVENTION

The present invention is defined in the appended independent claims. Preferred embodiments are defined in the dependent claims. In particular, the present invention concerns a biomarker panel for analyzing MSI loci in a biological sample, the panel comprising the following homopolymeric repeat regions as mapped to GRCh38/hg38 human reference genome:
  homopolymeric repeat comprising 11 consecutive adenines localized to human DIDO1 gene and starting at position chr20:62,905,340;
  homopolymeric repeat comprising 11 consecutive adenines localized to human MRE11 gene and starting at position chr11:94,479,765;
  homopolymeric repeat comprising 10 consecutive adenines localized to human SULF2 gene and starting at position chr20:47,657,577; and
  homopolymeric repeat comprising 8 consecutive adenines localized to human ACVR2A gene and starting at position chr2:147,926,117.

Equally importantly, the present invention concerns a method of analyzing MSI loci in a biological sample, comprising the step of:
  determining the number of nucleotides in the following homopolymeric repeats as mapped to GRCh38/hg38 human reference genome:
  homopolymeric repeat comprising 11 consecutive adenines localized to human DIDO1 gene and starting at position chr20:62,905,340;

homopolymeric repeat comprising 11 consecutive adenines localized to human MRE11 gene and starting at position chr11:94,479,765;

homopolymeric repeat comprising 10 consecutive adenines localized to human SULF2 gene and starting at position chr20:47,657,577; and homopolymeric repeat comprising 8 consecutive adenines localized to human ACVR2A gene and starting at position chr2:147,926,117.

In connection to the above, the present invention also concerns a kit for analyzing MSI loci in a biological sample, the kit comprising tools for amplifying nucleic acid regions comprising at least the above-mentioned homopolymeric repeats.

Finally, yet importantly, the present invention also concerns a cell or any other material, in particular genetic material, derived from a cell line HTC116 cl.110268743 that comprises one homonucleotide deletion in each of the above-mentioned homopolymeric repeats and in several advantageous other homopolymeric repeats. The cell line HTC116 cl.110268743 line was successfully deposited in accordance with the Budapest Treaty in BCCM/GeneCorner depository authority in Belgium under accession number LMBP 12278CB.

BRIEF DESCRIPTION OF FIGURES

For a fuller understanding of the nature of the present invention, reference is made to the following detailed description taken in conjunction with the accompanying drawings in which.

DETAILED DESCRIPTION OF THE INVENTION

Figure 1:
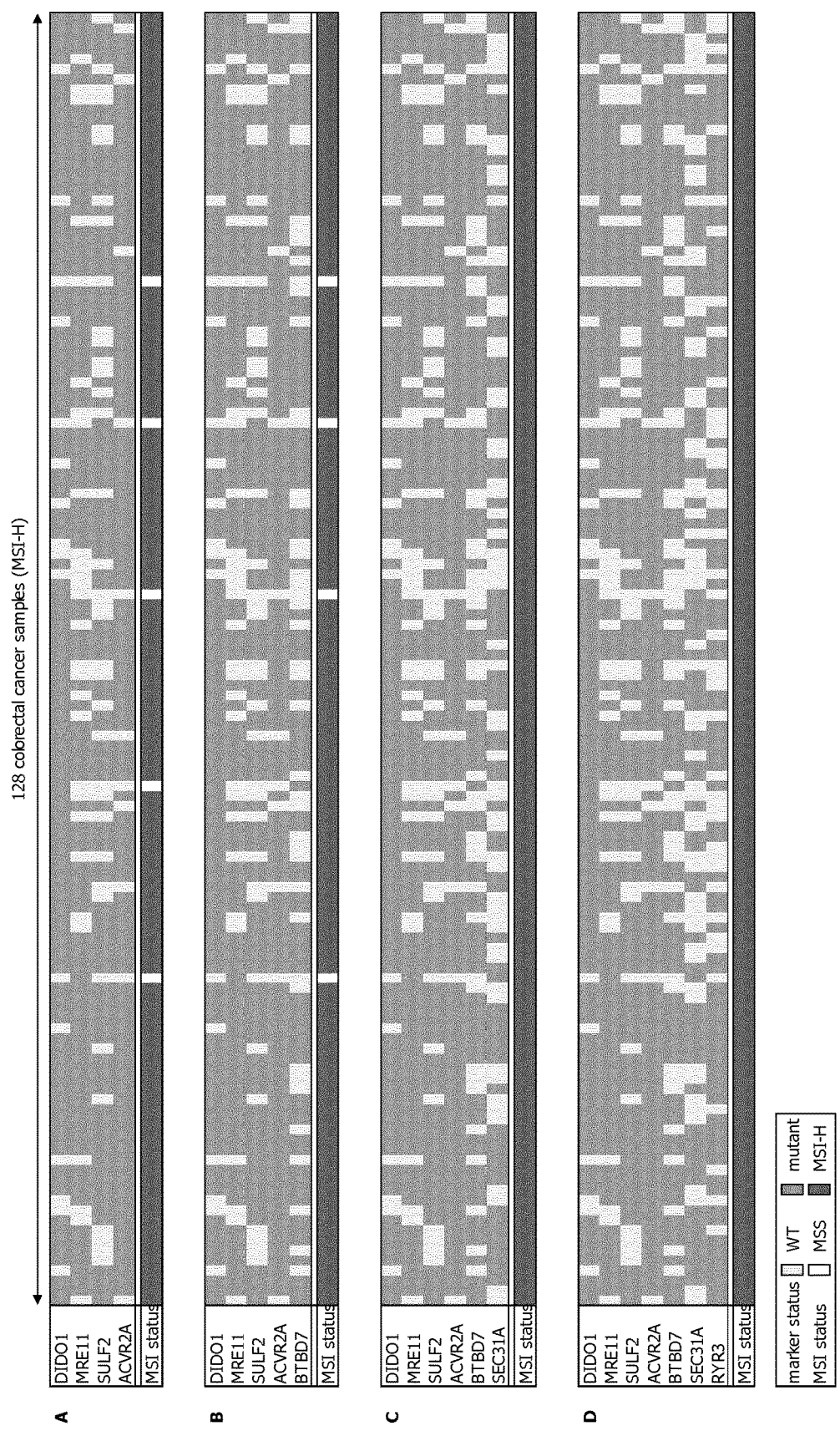
FIG. 1: shows the MSI status of 7 microsatellite markers (BTBD7, RYR3, SEC31A, ACVR2A, DIDO1, MRE11 and SULF2) in 128 MSI-H colorectal cancer samples. Different panels show MSI status (white, MSS; dark grey, MSI-H) when samples are evaluated for the minimal set of A) 4 markers and B), C) and D) sequentially adding a marker to the minimal set of 4 markers. Marker status for individual samples indicated as wild type (faint grey) or mutant (grey)
Figure 2:
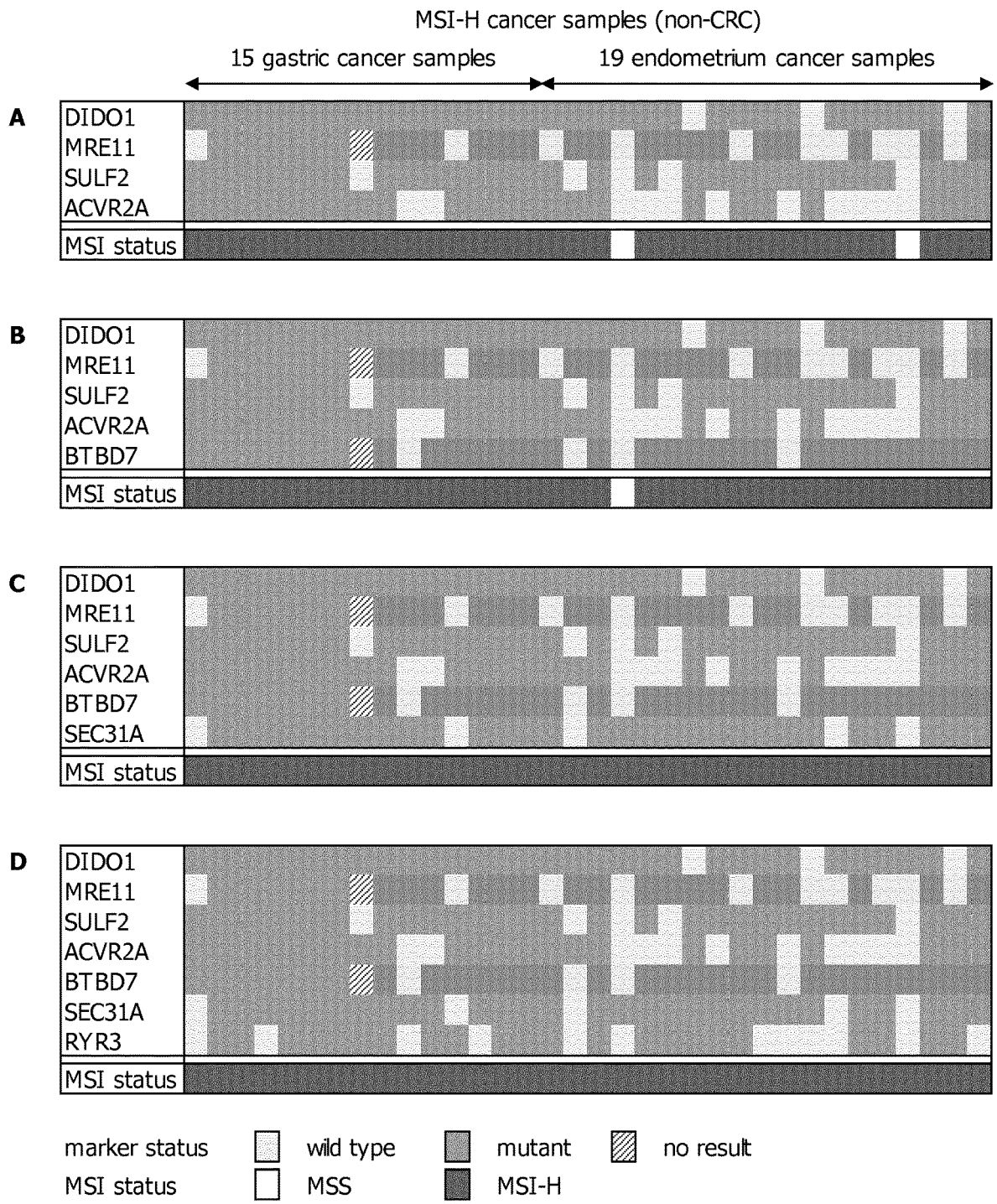
FIG. 2: shows the MSI status of 7 microsatellite markers (BTBD7, RYR3, SEC31A, ACVR2A, DIDO1, MRE11 and SULF2) in 15 MSI-H gastric cancer samples and 19 endometrium cancer samples. Different panels show MSI status (white, MSS; dark grey, MSI-H) when samples are evaluated for the minimal set of A) 4 markers and B), C) and D) sequentially adding a marker to the minimal set of 4 markers. Marker status for individual samples indicated as wild type (faint grey), mutant (grey) or no result (diagonal stripe).
Figure 3:
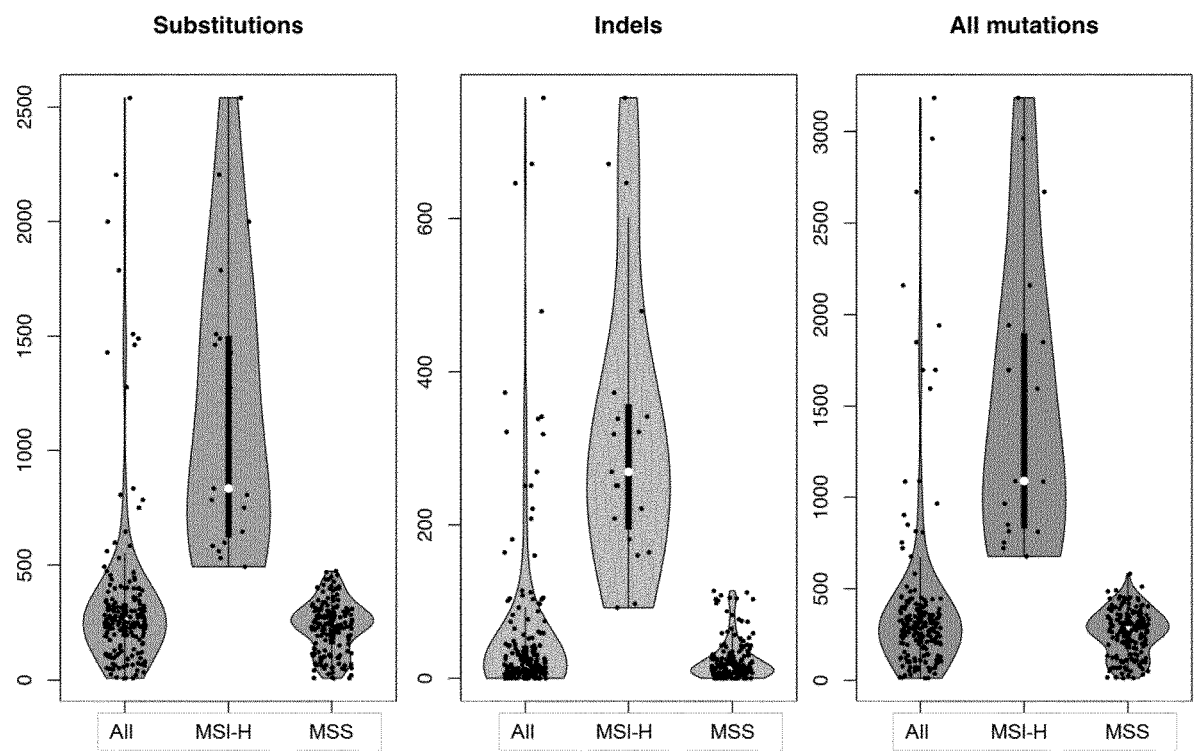
FIG. 3: Mutation load (measured by number of substitutions (left panel), number of indels (middle panel) or all mutations (right panel)) in 33 MSI-H versus 89 MSS samples
Figure 4:
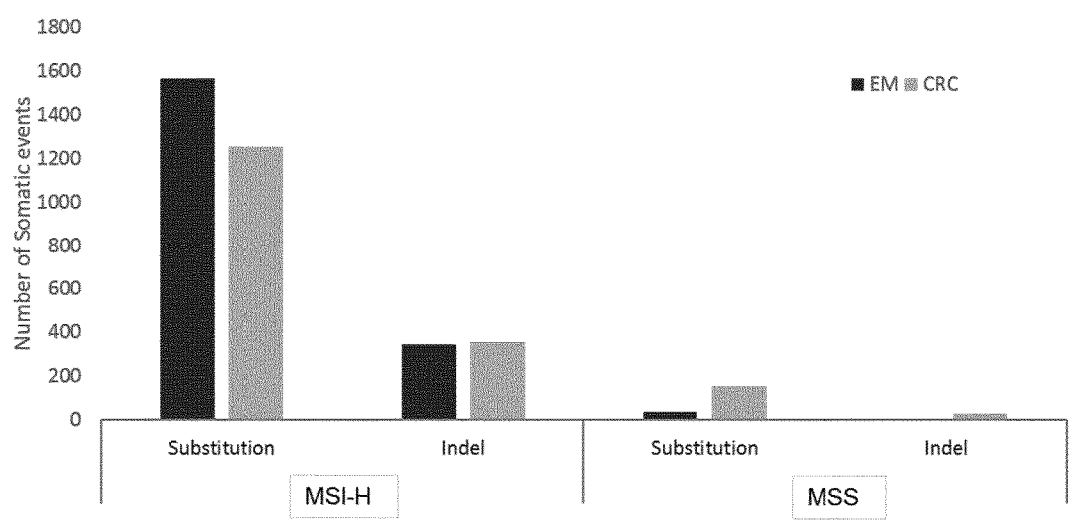
FIG. 4: Mutation load (measured by number of somatic events (substitutions and indels) in MSI-H versus MSS samples depending on cancer type. EM—endometrial, CRC—colorectal.

The present invention generally relates to a novel MSI biomarker panel, methods exploiting this panel, automated systems and kits for performing said methods, whereby the kits can preferably comprise or be provided in a form of a cartridge compatible with said automated systems and comprise tools and preferably also positive control material for detecting indels in said panel.

In a preferred embodiment, the invention provides a biomarker panel for analyzing MSI loci in a biological sample, the panel comprising at least the following homopolymeric repeat regions, or mutated forms thereof (whereby the mutation is the presence of at least one indel in the homopolymeric repeat sequence), as mapped to GRCh38/hg38 human reference genome:

homopolymeric repeat comprising 11 consecutive adenines localized to human DIDO1 gene and starting at position chr20:62,905,340;

homopolymeric repeat comprising 11 consecutive adenines localized to human MRE11 gene and starting at position chr11:94,479,765;

homopolymeric repeat comprising 10 consecutive adenines localized to human SULF2 gene and starting at position chr20:47,657,577; and homopolymeric repeat comprising 8 consecutive adenines localized to human ACVR2A gene and starting at position chr2:147,926,117.

We tested many randomly selected markers of the type as disclosed in WO2013153130 (VIB), which are homopolymers markedly shorter than the ones of the Bethesda panel. Random selections of a lower number of markers from the disclosed therein preferred set of 56 markers did not yield a robust assay capable of repeatedly detecting MSI-H phenotype over a large range of human cancer samples with minimal and most basic laboratory resources. The markers either could not be detected in a multiplex or even a duplex reaction or were varying in nucleotide number among different human ethnicities. Serendipitous choice of an exonic homopolymeric repeat comprising 8 consecutive adenines localized to human ACVR2A gene and starting at position chr2:147,926,117, which is not disclosed in the preferred set of 56 in WO2013153130, and the exonic homopolymeric repeat comprising 11 consecutive adenines localized to human MRE11 gene and starting at position chr11:94,479, 765, which is not disclosed in WO2013153130 at all, surprisingly lead to obtaining a highly performant panel for MSI detection in human MMR-deficient tumors.

We observed that the performance of the presented herein minimal panel of merely 4 markers surpasses the minimal acceptable performance set to 95% for correct identification of MSI-H-verified human colorectal cancer samples. As it is shown in the exemplary section below, we show that the above minimal panel of the invention could successfully recover 123 MSI-H positive samples out of the pool of 128 MSI-H CRC samples, which accounts for 96% of the samples being correctly identified as MSI-H. Thus, in a preferred embodiment, a panel is provided having performance of correctly identifying at least 90%, preferably at least 95% of MSI-H tumor samples.

Logically, addition of further markers can gradually increase this performance. Thus, in a preferred embodiment, the present invention provides the panel according to the previous embodiment, further comprising any one, two, or all of the following three homopolymeric repeat regions, or mutated forms thereof, as mapped to GRCh38/hg38 human reference genome:
homopolymeric repeat comprising 10 consecutive adenines localized to human BTBD7 gene and starting at position chr14:93,241,685;
homopolymeric repeat comprising 9 consecutive thymines localized to human SEC31A gene and starting at position chr4:82,864,412;
homopolymeric repeat comprising 10 consecutive adenines localized to human RYR3 gene and starting at position chr15:33,865,341.

The presented herein homopolymeric repeat markers that constitute the biomarker panel of the invention are merely short strings of at most 11 repeating homonucleotides, e.g. 11 consecutive adenines in DIDO1 3'UTR. As it will be appreciated by any person skilled in the art, complementary sequences thereto, e.g. 11 consecutive thymines complementary to the 11 consecutive adenines in DIDO1 3'UTR sequence, should also be construed as falling within the scope of the used herein above terms.

In a particularly preferred embodiment, the panel is provided comprising the five following homopolymeric repeat regions, or mutated forms thereof, as mapped to GRCh38/hg38 human reference genome:
homopolymeric repeat comprising 11 consecutive adenines localized to human DIDO1 gene and starting at position chr20:62,905,340;
homopolymeric repeat comprising 11 consecutive adenines localized to human MRE11 gene and starting at position chr11:94,479,765;
homopolymeric repeat comprising 10 consecutive adenines localized to human SULF2 gene and starting at position chr20:47,657,577;
homopolymeric repeat comprising 8 consecutive adenines localized to human ACVR2A gene and starting at position chr2:147,926,117; and
homopolymeric repeat comprising 10 consecutive adenines localized to human BTBD7 gene and starting at position chr14:93,241,685.

Using this core set of five markers 124 of 128, i.e. 97% of the tumor samples could be identified as MSI-H.

In another preferred embodiment, the panel is provided comprising the six following homopolymeric repeat regions, or mutated forms thereof, as mapped to GRCh38/hg38 human reference genome:
homopolymeric repeat comprising 11 consecutive adenines localized to human DIDO1 gene and starting at position chr20:62,905,340;
homopolymeric repeat comprising 11 consecutive adenines localized to human MRE11 gene and starting at position chr11:94,479,765;
homopolymeric repeat comprising 10 consecutive adenines localized to human SULF2 gene and starting at position chr20:47,657,577;
homopolymeric repeat comprising 8 consecutive adenines localized to human ACVR2A gene and starting at position chr2:147,926,117;
homopolymeric repeat comprising 10 consecutive adenines localized to human BTBD7 gene and starting at position chr14:93,241,685; and
homopolymeric repeat comprising 9 consecutive thymines localized to human SEC31A gene and starting at position chr4:82,864,412.

By further adding the additional marker localized in the SEC31A gene to the core set of markers, all of the 128 samples could be scored as MSI-H, making the panel even more efficient in defining the MSI status.

In a yet another preferred embodiment, the panel is provided comprising the seven following homopolymeric repeat regions, or mutated forms thereof, as mapped to GRCh38/hg38 human reference genome:
homopolymeric repeat comprising 11 consecutive adenines localized to human DIDO1 gene and starting at position chr20:62,905,340;
homopolymeric repeat comprising 11 consecutive adenines localized to human MRE11 gene and starting at position chr11:94,479,765;
homopolymeric repeat comprising 10 consecutive adenines localized to human SULF2 gene and starting at position chr20:47,657,577;
homopolymeric repeat comprising 8 consecutive adenines localized to human ACVR2A gene and starting at position chr2:147,926,117;
homopolymeric repeat comprising 10 consecutive adenines localized to human BTBD7 gene and starting at position chr14:93,241,685;
homopolymeric repeat comprising 9 consecutive thymines localized to human SEC31A gene and starting at position chr4:82,864,412; and
homopolymeric repeat comprising 10 consecutive adenines localized to human RYR3 gene and starting at position chr15:33,865,341.

A set of the above seven markers is calculated to reduce potential false negative rate to ~$1/1900$. Therefore, the addition of yet another marker compatible with the panels of the previous embodiments, provides a further performance safeguard, in particular for implementing the panel in detection of MSI in cancers other than colorectal, such as ovarian, endometrial, or gastric.

In a preferred embodiment, the biological sample originates from an individual suspected of having a tumor. In another embodiment, the biological sample is a tumor sample, possibly a fresh tissue or a fixed tumor sample, e.g. frozen or an FFPE sample. In a particularly preferred embodiment, the tumor is selected from colorectal, ovarian, endometrial or a gastric tumor. In another possible embodiment, the sample is a liquid biopsy sample. In another possible embodiment, the sample is any tissue sample, such as peripheral blood mononuclear cells (PBMCs) or other white bloodcells, or skin tissue, from a patient suspected of suffering from Lynch syndrome.

It is a further object of the invention to provide a method of analyzing MSI loci in a biological sample, the method comprising the step of determining the number of nucleotides in the biomarker panel of the above-described embodiments.

Therefore, in an embodiment of the invention, a method for analyzing MSI loci in a biological sample is provided comprising the step of:
  determining the number of nucleotides in the following homopolymeric repeats as mapped to GRCh38/hg38 human reference genome:
  homopolymeric repeat comprising 11 consecutive adenines localized to human DIDO1 gene and starting at position chr20:62,905,340;
  homopolymeric repeat comprising 11 consecutive adenines localized to human MRE11 gene and starting at position chr11:94,479,765;
  homopolymeric repeat comprising 10 consecutive adenines localized to human SULF2 gene and starting at position chr20:47,657,577; and homopolymeric repeat comprising 8 consecutive adenines localized to human ACVR2A gene and starting at position chr2:147,926,117.

For the same reasons as described above, in a preferred embodiment, the method of the invention further comprises determining the number of nucleotides also in any one, two, or all of the following homopolymeric repeat regions as mapped to GRCh38/hg38 human reference genome: homopolymeric repeat comprising 10 consecutive adenines localized to human BTBD7 gene and starting at position chr14:93,241,685;
homopolymeric repeat comprising 9 consecutive thymines localized to human SEC31A gene and starting at position chr4:82,864,412;
homopolymeric repeat comprising 10 consecutive adenines localized to human RYR3 gene and starting at position chr15:33,865,341.

In a particular embodiment, the method is provided comprising the step of:
  determining the number of nucleotides in the five following homopolymeric repeats as mapped to GRCh38/hg38 human reference genome:
homopolymeric repeat comprising 11 consecutive adenines localized to human DIDO1 gene and starting at position chr20:62,905,340;
homopolymeric repeat comprising 11 consecutive adenines localized to human MRE11 gene and starting at position chr11:94,479,765;
homopolymeric repeat comprising 10 consecutive adenines localized to human SULF2 gene and starting at position chr20:47,657,577;
homopolymeric repeat comprising 8 consecutive adenines localized to human ACVR2A gene and starting at position chr2:147,926,117; and
homopolymeric repeat comprising 10 consecutive adenines localized to human BTBD7 gene and starting at position chr14:93,241,685.

In a more specific embodiment, the method is provided comprising the step of:
  determining the number of nucleotides in the six following homopolymeric repeats as mapped to GRCh38/hg38 human reference genome:
homopolymeric repeat comprising 11 consecutive adenines localized to human DIDO1 gene and starting at position chr20:62,905,340;
homopolymeric repeat comprising 11 consecutive adenines localized to human MRE11 gene and starting at position chr11:94,479,765;
homopolymeric repeat comprising 10 consecutive adenines localized to human SULF2 gene and starting at position chr20:47,657,577;
homopolymeric repeat comprising 8 consecutive adenines localized to human ACVR2A gene and starting at position chr2:147,926,117;
homopolymeric repeat comprising 10 consecutive adenines localized to human BTBD7 gene and starting at position chr14:93,241,685; and
homopolymeric repeat comprising 9 consecutive thymines localized to human SEC31A gene and starting at position chr4:82,864,412.

In another specific embodiment, the method is provided comprising the step of:
  determining the number of nucleotides in the seven following homopolymeric repeats as mapped to GRCh38/hg38 human reference genome:
homopolymeric repeat comprising 11 consecutive adenines localized to human DIDO1 gene and starting at position chr20:62,905,340;
homopolymeric repeat comprising 11 consecutive adenines localized to human MRE11 gene and starting at position chr11:94,479,765;
homopolymeric repeat comprising 10 consecutive adenines localized to human SULF2 gene and starting at position chr20:47,657,577;
homopolymeric repeat comprising 8 consecutive adenines localized to human ACVR2A gene and starting at position chr2:147,926,117;
homopolymeric repeat comprising 10 consecutive adenines localized to human BTBD7 gene and starting at position chr14:93,241,685;
homopolymeric repeat comprising 9 consecutive thymines localized to human SEC31A gene and starting at position chr4:82,864,412; and
homopolymeric repeat comprising 10 consecutive adenines localized to human RYR3 gene and starting at position chr15:33,865,341.

In possible embodiments, the method of the invention may further comprise a step of diagnosing the MSI status of the biological sample if an indel is detected in at least two of the homopolymeric repeats.

Preferably, the methods of the invention are provided wherein the biological sample obtained from a subject is a tumor or a potential tumor sample. In principle, the disclosed herein methods can be performed using any confirmed or potential tumor sample. In a preferred embodiment, the tumor is a colorectal, gastric, ovarian, or endometrial tumor.

As it will be appreciated by persons skilled in the art, the nature of the homopolymeric repeat marker panel of the invention determines that the methods of the invention will preferably be performed using genomic DNA present in the biological samples. Depending on the sample type, in a preferred embodiment the method of the invention preceded by any of the following steps:
  liberating and/or isolating the nucleic acid potentially comprising the target sequence from the source of a nucleic acid, providing said liberated and/or purified nucleic acid potentially comprising the target to the step of amplifying said nucleic acid As genomic DNA is a rich and complex nucleic acid material, it is advantageous that the sequences flanking the homopolymeric repeat regions as defined above are amplified prior to the step of determining the number of nucleotides therein. Thus, in a preferred embodiment, the method is provided further comprising the step of:

amplifying nucleic acid regions comprising the homopolymeric repeats as listed above. As it will be apparent to any skilled person, such amplifying will results in amplification products comprising the homopolymeric repeat sequence irrespective of its MSI status. That is such amplification products may comprise the wild type (WT) version of a given homopolymeric repeat or its MSI variant, i.e. a mutant comprising an indel of at least one homonucleotide in the homopolymeric repeat Sequence.

Naturally, in an obvious embodiment, the amplification is preferably performed by polymerase chain reaction (PCR), e.g. using a means for performing PCR, such as appropriate reagents and/or gear including a thermocycler. However, other amplification techniques as known in the art can also be used. These include but are not limited to Loop Mediated Isothermal Amplification (LAMP), Nucleic Acid Sequence Based Amplification (NASBA), Strand Displacement Amplification (SDA), Multiple displacement amplification (MDA), Rolling Circle Amplification (RCA), Ligase Chain Reaction (LCR), Helicase dependent amplification (HDA), or Ramification amplification method (RAM).

In a preferred embodiment, the method is provided wherein the step of amplifying comprises use of at least one primer having sequence identified by any of the following SEQ ID NO.:1-14:

For DID01 marker:
SEQ ID NO.: 1
TAGCGTGTGAATCGGACAT

SEQ ID NO.: 2
TTGACTGGGCAGATAGGGGA

For MRE11 marker:
SEQ ID NO.: 3
ATAGTTCACCCATGGAAACC

SEQ ID NO.: 4
GGAGGAGAATCTTAGGGAAA

For BTBD7 marker:
SEQ ID NO.: 5
ACTGGACTCCCGCTGG

SEQ ID NO.: 6
CGCTCAGCCTCCATAAATC

For SULF2 marker:
SEQ ID NO.: 7
CAACTTCATTTCTTTTCAGTACCTT

SEQ ID NO.: 8
CTGTCCAGATACCATTTCTC

For ACVR2A marker:
SEQ ID NO.: 9
AGCATCCATCTCTTGAAGACAT

SEQ ID NO.: 10
GCATGTTTCTGCCAATAATCTCT

For SEC31A marker:
SEQ ID NO.: 11
CAACTTCAGCAGGCTGT

SEQ ID NO.: 12
AGTCTGAGAAGCATCAATTTT

For RYR3 marker:
SEQ ID NO.: 13
CATTTTCTAAATGCCTCCCTTAAA

SEQ ID NO.: 14
GTCCATTAGGCACAAAAAG

In a more specific embodiment, the step of amplifying comprises use of at least one primer pair selected from the following: SEQ ID NO.:1 and SEQ ID NO.:2; SEQ ID NO.:3 and SEQ ID NO.:4; SEQ ID NO.:5 and SEQ ID NO.:6; SEQ ID NO.:7 and SEQ ID NO.:8; SEQ ID NO.:9 and SEQ ID NO.:10; SEQ ID NO.:11 and SEQ ID NO.:12; or SEQ ID NO.:13 and SEQ ID NO.:14.

As it will be appreciated by any skilled person, depending on amplification conditions, the above-listed primer sequences will likely work also in case 1, 2 or in some instances even possibly 3 nucleotides are altered in them, i.e. added, deleted, or replaced by a different nucleotide or a modified nucleotide. Thus, in a possible embodiment, the present invention also provides at least one primer sequence identified by any of the above SEQ ID NO.:1-14, wherein 1, 2, or 3 nucleotides are altered. In an alternative embodiment, the present invention also provides at least one primer sequence being at least 80%, preferably at least 85%, more preferably at least 90%, or most preferably at least 95% identical to any of the above SEQ ID NO.:1-14. As it will be appreciated by skilled persons, in order to generate amplicons covering the homopolymeric repeat regions of interest, alternative primers can be designed 5-, 10, 20, 50, or 100 nucleotides upstream or downstream with respect of to the positions of the above-described primer pairs. Thus, such alternative primer pairs should also be regarded as an alternative obvious embodiment of the present invention.

The provided herein method has the advantage of being fully automatable and adaptable to any standard quantitative PCR thermocycling instrument, which allows it to be performed by a regular laboratory personnel without the need of specialized training. In addition to the above, the method is highly sensitive, multiplexing-suitable, can provide an estimate of the relative amounts of the detected homopolymeric nucleotide repeat sequences and the variants thereof. Therefore, in a possible embodiment, the PCR can be a quantitative or semi-quantitative PCR.

As the methods of the invention concern detection of changes in the number of homonucleotides in a string of very short (i.e. <12 nt) homonucleotide repeat sequences, it is advantageous they are highly specific. For example, during amplification of homopolymeric repeat regions, polymerase slippage is known to occur. This leads to mistakes in copying the original number of repeated nucleotides, causing the accumulation of artificial deletions or insertions in the amplified PCR product. Therefore, in a preferred embodiment, the step of amplifying is performed using a proofreading polymerase, i.e. a polymerase having 3'-5' exonuclease activity. Many such PCR-grade polymerases are known and commercially available. Examples include but are not limited to polymerases like Q5, Pfx, Pfu, Ex Taq etc.

In most preferred embodiments, melting curve analysis of the amplified nucleic acid products is used in the step of determining the number of nucleotides. Therefore, in a particularly advantageous embodiment of the methods of the invention, the step of amplifying results in generating melting curve data.

Melting or melt curve analysis is an assessment of the dissociation or association-characteristics of a double-stranded nucleic acid molecule during temperature variation. Consequently, the melting curve data is to be understood as any captured data representing either dissociation or association characteristics of the nucleic acid molecule under investigation such as the target product of a nucleic acid amplification. The melting curve data can be obtained by including appropriate fluorescent moieties in samples under investigation that are processed by any instrument or a method for conducting amplification such as thermal cycling, PCR, quantitative PCR etc. It can be obtained from any apparatus equipped with a means of adjusting the sample temperature to above the melting temperature of the DNA sample, which is equipped with known fluorometric or spectrophotometric means. Examples of such instruments include, but are not limited to, regular optical thermocyclers commonly used for qPCR or fluorometers with temperature control, etc.

Melting curve analysis and high resolution melting (HRM) analysis are commonly used methods for detecting and analyzing the presence of nucleic acid sequences in a sample. One way of monitoring dissociation and association characteristics of a nucleic acid happens with the aid of dyes. The detection chemistries used for qPCR and melt curve analysis rely on (a) chemistries that usually detect fluorescence of a target-binding dye, e.g. a DNA-binding fluorophore such as LC Green, LC Green+, Eva Green, SYTO9 CYBR Green, or (b) target specific chemistries that usually utilize fluorophore-labeled DNA probes, such as e.g. beacon probes, and/or primers, such as e.g. scorpion primers. It is well known in the art that other detection chemistries can be applied in melt curve analysis.

In one embodiment of the invention, the amplification products are heated in the presence of one or more intercalating dyes during a melting curve test procedure. The dissociation of the DNA during heating is measurable by the large reduction in fluorescence that results. In another particular embodiment, the amplification products are heated in the presence of one or more dye-labeled nucleic acid, e.g. one or more probes, during a melting curve test procedure.

In the case of the probe-based fluorescence melting curve analysis, variation detection in nucleic acids is based on melting temperature generated by thermal denaturation of the probe-target hybrid. As heating of the generated amplicons proceeds, the changes in the strength of the signal are detected in function of temperature, typically over a temperature interval, to obtain melting curve raw data.

In preferred embodiments of the methods of the invention, the amplifying comprises use of a probe. In principle, in possible embodiments, any target-specific oligonucleotide probe suitable for performing melting curve analysis can be used. Preferred known probes may comprise a pair consisting of a fluorophore and a quencher, and may also advantageously form secondary structures such as loops or hairpins.

Particularly preferred are the molecular beacon probes, or molecular beacons, which are hairpin shaped molecules with an internally quenched fluorophore whose fluorescence is restored when they bind to a target nucleic acid sequence. For this reason, molecular beacons are not degraded by the action of polymerase and can be employed in studying their hybridization kinetics to their target via melting curve calling. A typical molecular beacon probe is about 20, preferably 25 nucleotides long or longer. Typically, the region that is complementary to and binds to the target sequence is 18-30 basepairs long. The structure and working mechanism of molecular beacons is well known in the art.

Therefore, in a particularly preferred embodiment, the method is provided wherein the step of amplifying comprises a use of at least one molecular beacon probe.

In a preferred embodiment of the above embodiment, the molecular beacon probe comprises a sequence identical to or complementary to the mutant homopolymeric nucleotide repeat sequence comprising a deletion of at least one homonucleotide in the target homopolymeric nucleotide repeat sequence. Such molecular beacon design allows to detect with high sensitivity and specificity the selected mutated MSI marker, while at the same time remaining sufficiently sensitive to the wild-type (i.e. expected) marker. It should be remarked that with the term "target homopolymeric nucleotide repeat sequence" it is meant the wild-type or reference homopolymeric repeat sequence as it is expected in the conditions where no MSI is present. Conversely, by "mutant homopolymeric nucleotide repeat sequence" it is meant a homopolymeric nucleotide repeat sequence comprising an insertion or a deletion of at least one homonucleotide in the homopolymeric repeat sequence. The variance will then be measured between the raw melting data of the wild type and the mutant and will be characteristic of the melting curve raw data.

In a specific embodiment, the method is provided wherein the at least one molecular beacon probe has a sequence identified by any one of the following SEQ ID NOs.:

```
For DIDO1 marker:  SEQ ID NO.: 15  CGCACGACATGGAAAAAAAAAATCCGTGCGTAAA

For MRE11 marker:  SEQ ID NO.: 16  CGTCGAACCTTAAAAAAAAAAGTTACCGACGAA

For BTBD7 marker:  SEQ ID NO.: 17  CGCACGACTTATTAAAAAAAAATGACAGTGCGTAAA

For SULF2 marker:  SEQ ID NO.: 18  CGTCGGTACCTTAAAAAAAAACATCACGACGAA

For ACVR2A marker: SEQ ID NO.: 19  GTGCATAAAAAAAGAGCACTAAA

For SEC31A marker: SEQ ID NO.: 20  CGCACTTGCCAAAAAAAATTGATGGTGCGTAAA

For RYR3 marker:   SEQ ID NO.: 21  CGTCGCCCTTAAAAAAAAACTGCCGACGAA
```

In a possible embodiment, the at least one molecular beacon probe is provided having a certain degree of sequence variation with respect to the above SEQ ID NOs. 15-21. Such variation could account for the use of different beacon stem sequence (underlined and in italics above), or be due to removing or adding nucleotides to the hybridizing part of the beacon that is specific for the sequence to be detected (indicated in bold above). The latter could include adding or removing at 1 or 2 nucleotides from the homopolymeric repeat sequences, or including more or less nucleotides in said repeat's flanking sequence.

Because of the thus conferred specificity of a given molecular beacon probe to one homopolymeric repeat marker and the unstable (mutant) variants thereof, it is also possible to design a multiplexing assay, wherein at least two, possibly more molecular beacon probes are used in one reaction tube or compartment.

Therefore, in another preferred embodiment, the method is provided wherein the step of amplifying comprises at least one duplex amplification of a pair of homopolymeric repeats, said pair being selected from the following combinations:

duplex amplification of
the homopolymeric repeat comprising 11 consecutive adenines localized to human DIDO1 gene and starting at position chr20:62,905,340 together with
the homopolymeric repeat comprising 11 consecutive adenines localized to human MRE11 gene and starting at position chr11:94,479,765;
duplex amplification of
the homopolymeric repeat comprising 8 consecutive adenines localized to human ACVR2A gene and starting at position chr2:147,926,117;
together with
the homopolymeric repeat comprising 9 consecutive thymines localized to human SEC31A gene and starting at position chr4:82,864,412; and
duplex amplification of
the homopolymeric repeat comprising 10 consecutive adenines localized to human BTBD7 gene and starting at position chr14:93,241,685;
together with
homopolymeric repeat comprising 10 consecutive adenines localized to human SULF2 gene and starting at position chr20:47,657,577.

In particularly advantageous embodiments that highly improve the robustness of the methods of the invention, in particular when multiplexing is used, a novel approach is used wherein a wavelet transform function is applied on the raw melting curve data.

Wavelets are mathematical functions that cut up data into different frequency components, and then study each component with a resolution matched to its scale. These basis functions are short waves with limited duration. The basis functions of the wavelet transform are scaled with respect to frequency. There are many different wavelets that can be used as basis functions. The basis function ~(t), also called the mother wavelet is the transforming function. The term mother implies that the functions with different region of support that are used in the transformation process are derived from one main function, or the mother wavelet. In other words, the mother wavelet is a prototype for generating the other window functions. In general, the wavelet ψ(t) is a complex valued function. A general wavelet function is defined as:

$$\psi s,\tau(t)=|s|^{-1/2}\psi[(t-\tau)/s]$$

This shift parameter 'τ' determines the position of the window in time and thus defines which part of the signal x(t) is being analyzed. In wavelet transform analysis, frequency variable 'ω' is replaced by scale variable 's' and time shift variable is represented by 'τ'.

The wavelet transform utilizes these mother wavelet functions, and performs the decomposition of the signal x(t) into weighted set of scaled wavelet functions ψ(t). The main advantage of using wavelets is that they allow to capture a characteristic and unique signature of a given larger and more complex dataset without resulting in the loss of data.

For example, two large raw melting curve datasets obtained from two amplification products differing only by one nucleotide in length, are highly similar but after applying a wavelet transform will produce two distinct signatures. Such signatures will then be easier to compare against one another in order to consistently conclude that there was an insertion or deletion present in one of the amplification products. In conclusion, application of the wavelet function results in noise reduction and increase in computational efficiency and speed when dealing with large and similar datasets. As a consequence, wavelet-processed data is particularly suitable for classifying samples involving combined analysis of several multiplexed targets within one experiment, especially when there are large raw datasets generated that require discrimination of minute data variations.

The currently existing methods for MSI detection suffer from the following disadvantages:
(a) to determine repeat length they either require additional specialized equipment for performing post-PCR analysis and/or this analysis typically needs to be interpreted by a highly trained expert; or
(b) in case of high-resolution melting curve with dsDNA-intercalating dyes, the disadvantage is the very limited multiplexing capacity in order to avoid overlapping melting signals from different amplicons, and further, it provides no ability to quantify the relative amounts of instable (mutant) sequences to the stable (wild-type) ones. We observed that applying discrete wavelet transform on the melting curve data leads to very robust and consistent interpretation of results in a fully automated manner and thus overcomes these drawbacks.

Thus, in a preferred embodiment, the method of the invention further comprises the steps of:
(a) applying wavelet transform on the melting curve data; and
(b) using the results obtained from (a) in determination of the number of nucleotides in any of the homopolymeric repeats as listed above. In other words, in an embodiment, methods are provided that apply wavelet transform functions to analyze melting curve data of nucleic acids from a test sample for determining a presence or an absence of an indel in each of the homopolymeric repeats from the biomarker panel of choice, which information then can be used to classify said test sample as having MSI or not.

In a preferred embodiment, the melting curve data is raw meting curve data, i.e. data representing the raw metrics of a signal obtained from a nucleic acid dissociation or association experiment. In other words, such raw metrics are not mathematically processed by e.g. applying first or second derivative melting curve analysis, as it is frequently done in the art, but following their collection by a detector, they are sent to a computer wherein the wavelet transform function is applied to them.

In a most preferred embodiment, the wavelet transform is a discrete wavelet transform or "DWT". DWT is any wavelet transform for which the wavelets are discretely sampled. As with other wavelet transforms, a key advantage it has over Fourier transforms is temporal resolution: it captures both frequency and location information (location in time). Application of the discrete wavelet transform on the raw metrics produces a set of reconstruction output wavelet coefficients at different scales: (a) one is the approximation output which is the low frequency content of the input signal component and (b) the other is the multidimensional output which gives the high frequency components, being the details of the input signal at various levels. These coefficients are further referred to as discrete wavelet transform coefficients or dwt coefficients. The separation of features into different scales (or frequencies) allows for an operator or computer algorithm to select the dwt coefficients most relevant for certain decisions or analysis, a process often referred to as wavelet filtering. This process can be applied repeatedly, splitting up the signal in multiple frequency bands. When applied on melting curve data, the highest frequency wavelet coefficients are mostly noise whereas the lowest resolution coefficients capture information related to instrument gain or amplification efficiency in the preceding amplification reaction. Both have little or no relevance for the identification of a specific oligonucleotide in a sample subject to melting curve analysis itself but potentially have relevance with respect to reliability of such identification. Packages containing all functions necessary for computing and plotting DWTs have been described (Aldrich, 2015) and will be known to skilled programmers and mathematicians.

In a preferred embodiment of the method, the step of performing discrete wavelet transform on the melting curve data to produce dwt coefficients, will in a particular setting calculate a one-dimension (1D) wavelet transform of the raw data or the reduction data using a mother wavelet from the Daubechies family. The mother wavelet is the unmodified wavelet chosen as basis for the discrete wavelet transform (Daubechies, 1992). Good results were obtained when the DB8 mother wavelet was used. Additional tests with DB4 and Haar mother wavelets also provided highly satisfying performance, the results of which can be provided on request. Based on the latter, we believe that other existing mother wavelets can also be suitable. The mother wavelet may and preferably is subsequently dilated, shifted and scaled, using the pyramid dwt algorithm, to generate a set of child wavelets that best represent the fluorescence melting curve signal to be analyzed; the set of wavelet and scale coefficients obtained from the algorithm being the result of the discrete wavelet transform. In the specified example, boundary conditions for the DWT are periodic. The raw data input to the transform can be the entire data measured or its subset that covers all significant events of a given experiment.

In line with the above, in order to produce dwt coefficients, the methods of the present invention may apply the discrete wavelet transform on the raw melting curve data, or on a mathematically-transformed or reduced melting curve data, i.e. only on a selection of raw data.

Furthermore, not all dwt coefficients need to be always used for the final determination of the nucleotide number. For increasing computational speed, only a selection of dwt coefficients may suffice. Preferably, the discrete wavelet transform is performed on raw melting curve data. Optionally however, data reduction can be performed on the raw data in accordance with any mathematical method known in the art to generate a selection of raw data. In the latter case, the discrete wavelet transform will be applied on said selection of raw data to also produce dwt coefficients. In summary, in a particular embodiment, the results obtained from (a) can be dwt coefficients obtained from raw meting curve data. In an alternative embodiment, the results obtained from (a) can be dwt coefficients obtained from a selection of raw melting curve data. In a yet another specific embodiment, the results obtained from (a) may be a selection of dwt coefficient obtained from either of the above alternative embodiments.

In one particular embodiment, the discrete wavelet transform is a 1D discrete wavelet transform. In an even more specific embodiment, the 1D discrete wavelet transform is a 1D Daubechies wavelet transform.

In order to apply a discrete wavelet transform, a mother wavelet needs to be chosen. In a further preferred embodiment, the Daubechies discrete wavelet transform is applied, which uses a mother wavelet from the Daubechies family, most preferably being the DB8 mother wavelet or DB4 or Haar mother wavelet.

In principle, in alternative possible embodiments, any wavelet transform function suitable for generating significant coefficients that capture information allowing discrimination at the single nucleotide level can be used in the method of the invention. Possible examples include the Haar wavelet (which can also be considered part of the Daubechies family), least assymetric, coiflet, or best localized. Alternative embodiments can use alternative algorithms to calculate the dwt including the lifting algorithm or the dual-tree complex wavelet transform. Other forms of discrete wavelet transform include the non- or undecimated wavelet transform, wherein downsampling is omitted, or the Newland transform, wherein an orthonormal basis of wavelets is formed from appropriately constructed top-hat filters in frequency space. Other examples possibly exist and will be readily applicable to the disclosed herein methods by an appropriately skilled person.

One of the major advantages of the methods of the invention is their straightforward automation and adaptation, especially to known standard qPCR systems. Therefore, in a particular embodiment a method is provided wherein determining the number of nucleotides in the above-listed homopolymeric repeats is performed in an automated manner, e.g. by a software. This could be done on an automated system for example equipped with appropriate hardware and software arrangements that can read the signals obtained from the methods of the invention, analyze them, and provide a conclusion with regard to the presence or absence of an indel in the marker of choice from a given sample. A particularly suitable system for such automation is the Biocartis Idylla™ platform, which in addition to performing PCR and providing interpretation of its results, also fully automates the entire sample processing and nucleic acid isolation workflow. Consequently, in a possible embodiment, the present invention provides a fully automated sample-to-result method for analyzing MSI loci.

In a yet another attractive embodiment of the invention, the method is performed wherein the determining the number of nucleotides in any of the above-listed homopolymeric repeats is further also performed in a control biological sample. Such a control or reference standard sample could e.g. be a material derived from an MSI-H tumor confirmed to have an indel in any of the above-listed homopolymeric repeats of choice, or a synthetic or isolated nucleic acid construct, e.g. a plasmid. A particularly advantageous reference standard could be e.g. one of Acrometrix standards, which contains a mix of both synthetic and genomic DNA. The technology uses a very highly characterized and sequenced cell line GM2438 as genomic background DNA into which sequenced synthetic targets are spiked in. In the Acrometrix approach, these targets are linear synthetic DNA molecules comprising a sequence mimicking an alteration associated with e.g. a biomarker of choice, which in the context of the present invention it could be a sequence of any of the above-described homopolymeric repeats comprising an indel, preferably for PCR-purposes together with their flanking sequences. The targets further comprise a "tail"

sequence coupled to the above-described alternation-mimicking sequence, which further serve identification and quantification purposes. The resulting sequence is considered to be a hybrid sequence, comprising the alteration-mimicking sequence and the tail sequence. The tail e.g. may be mimicking a known alteration such as a SNP in a gene for which detection assays are available, and therefore it can provide an additional means for indirectly for absolutely quantifying the alteration-mimicking sequence, like in this case, an indel in the marker or markers of choice. Such standard could be e.g. be useful for verification and validation purposes, for example in case a further NGS investigation would be envisaged, especially that current NGS approaches still tend to miss information about indels in homopolymeric repeat sequences.

Alternatively, in a preferred embodiment of the invention, the control biological sample comprises material derived from HTC116 cl.110268743 cell line that was generated for the purposes of the present invention and deposited under the Budapest Treaty on 28 Nov. 2017 in the BCCM/GeneCorner depository authority in Belgium with the accession number LMBP 12278CB. The cell line comprises one homonucleotide deletion in each of the above-mentioned homopolymeric repeats. This means that the genome of the cell line contains the following mutant (i.e. MSI variant) homopolymeric repeats:

10 adenines localized to human DIDO1 gene and starting at position chr20:62,905,340;

10 adenines localized to human MRE11 gene and starting at position chr11:94,479,765;

9 adenines localized to human SULF2 gene and starting at position chr20:47,657,577;

7 adenines localized to human ACVR2A gene and starting at position chr2:147,926,117;

9 adenines localized to human BTBD7 gene and starting at position chr14:93,241,685;

8 thymines localized to human SEC31A gene and starting at position chr4:82,864,412; and 9 adenines localized to human RYR3 gene and starting at position chr15:33,865,341.

In addition, the cell line also contains an indel for several other MSI-associated repeats, e.g. BAT25 and BAT26 from the Bethesda panel, which can be used in comparative studies.

In a related aspect, the present invention also provides a cell or any other material, in particular genetic material, that is derived from the cell line HTC116 cl.110268743. Such material could be isolated genomic DNA or a cell lysate. Other appropriate forms of such material will be obvious to the skilled person depending on the final design of the provided herein methods and kits based on said methods.

In further aspect, the present invention also provides kits for detecting indels in the MSI biomarker panel of the invention or for performing the method according to the invention. In a particular embodiment, the present invention provides a kit for analyzing MSI loci in a biological sample, the kit comprising tools for detecting nucleic acid regions comprising the above-described homopolymeric repeats as provided in the biomarker panel of the invention. Preferably said tools are sequence-specific, i.e. are designed to recognize in a sequence specific-manner said homopolymeric repeats with their flanking regions of selected length. In a preferred embodiment, the sequence-specific tools comprise a primer or a primer pair or a probe capable of hybridizing to the region comprising the homopolymeric repeat. For example, such tools may preferably comprise a primer hybridizing to a region upstream or downstream of the repeat and designed to generate in an amplification reaction an amplification product comprising at least one of said homopolymeric repeats or their mutated versions e.g. comprising one or two homonucleotides less or more as compared to the wild type homopolymeric repeat version. In another example, the tools may comprise a probe capable of hybridizing to any of said homolymeric repeat sequences (or its indel-comprising mutated versions) and to at least one directly flanking region (i.e. upstream or downstream, but preferably both) of said repeat sequence. In a specific embodiment, the tools comprise at least one primer or primer pair selected from SEQ ID NOs.: 1-14. In an alternative specific embodiment, the tools comprise at least one molecular beacon probe selected from SEQ ID NOs.: 15-21. In a possible embodiment, the tools comprise at least one primer or primer pair selected from SEQ ID NOs.: 1-14 and at least one molecular beacon probe selected from SEQ ID NOs.: 15-21. The tools may further comprise e.g. a proofreading polymerase, appropriate buffering systems, dNTPs, a selection of dyes possibly with compatible quenchers etc. In further embodiment, the kit is provided comprising control biological sample material, preferably being the material derived from HTC116 cl.110268743 cell line In a preferred embodiment, a kit is provided further comprising a cartridge. Possibly, the kit can be provided in a form of a cartridge. Thus, advantageously, the present invention provides a kit wherein said tools for detecting nucleic acid regions comprising the above-described biomarker panel homopolymeric repeats are provided in a cartridge engageable with an automated system. As described above, a suitable example of a cartridge and an automated system engageable therewith is the Biocartis Idylla™ platform. Further details of this and similarly applicable to the present invention systems can be found in WO2007004103, EP1896180, EP1904234, and EP2419705. As can be appreciated from the cited herein documents, advantageous cartridges not only comprise means for performing PCR but also may be designed to directly accept a source of nucleic acid or a sample, isolate or liberate nucleic acids from said nucleic acid source, and provide (e.g. by pumping) the thus liberated nucleic acid for the subsequent PCR-based assay.

In a preferred embodiment, the tools, such as primers, probes, and/or other reagents including the proofreading polymerase, can be provided in said cartridge in a spotted format, which contributes to increased shelf life.

In a further aspect related, the present invention also provides automated systems for detecting indels in the MSI biomarker panel in accordance with the methods of the invention and/or for processing kits according to the invention.

In a possible embodiment, such automated system can comprise a console and an instrument compatible with the reusable cartridges of the invention. The instrument comprises control modules for performing assays. The console is a computer to control and monitor the instrument's actions and the cartridge status during the assays. The assay will preferably be entirely run inside of the cartridge and may include for example a real-time PCR. After inserting a sample in such cartridge of the invention that is pre-loaded with reagents as described above, the cartridge is loaded into the instrument and the instrument controls the assay which is performed autonomously in the cartridge. After the assay was run, the console software processes the results and generates a report accessible for the end-user of the automated system.

The automated system can be an open or a closed automated system. After a sample was added or inserted into the cartridge, the cartridge is fed into the system, which is then closed and stays closed during the operation of the system. The closed system contains all the necessary reagents on board, so the closed configuration provides the advantage that the system performs contamination-free detection. Alternatively, an open, accessible cartridge can be used in an automated system. The necessary reagents are added in the open cartridge as required, thereafter a sample can be inserted in the open cartridge and the cartridge can be run in a closed, automated system.

Preferably, cartridge-based systems containing one or more reaction chambers and one or more fluid chambers are used. Some of the fluid chambers may hold fluid which is used for producing a lysate from the sample. Other chambers may hold fluids such as reaction buffers, washing fluids and amplification solutions. The reaction chambers are used to perform the different steps of the detection such as washing, lysis and amplification.

In a particularly desired embodiment in accordance with the above-listed embodiments, to streamline and facilitate the interpretation of the results of the method according to present invention, the analysis on the melting curve is also performed in an automated manner by means of a computer-implemented method.

Lastly, it is also the object of present invention to provide a use of the biomarker panels, methods, kits including cartridges, and automated systems according to the invention, in analyzing MSI loci in a tumor sample or a biological sample expected to comprise tumor material.

In a preferred embodiment, the tumor is a colorectal cancer (CRC). In an alternative embodiment, the tumor is an ovarian or an endometrial cancer. In a yet another embodiment, the tumor is a gastric cancer.

In a possible embodiment, the invention also provides a use of the biomarker panels, methods, kits including cartridges, and automated systems according to the invention, in analyzing MSI loci in a tumor sample and in predicting the response to immunotherapy of the subject from whom the tumor sample was derived, based on the analysis. The latter use can be envisaged in view of the recent reports from literature, notably Turajlic et al., 2017, Lancet Oncology, wherein increased accumulation of indels in the genome was shown to correlate with generation of novel open reading frames encoding for a large quantity of neoantigenic sequences. In line with this, in continuation we demonstrate that detection of at least 2 or 3 indels in the biomarker panel of the invention strongly correlates with the total number of indels and neoantigens scored per sample. Our data further show that a distinct immunogenic phenotype of a tumor can be predicted by methods and/or kits of the invention. The latter is very promising for the following reasons. Immune checkpoint blockade was recently approved for the treatment of unresectable or metastatic, microsatellite-instability-high (MSI-H) tumors regardless of site or histology. Observed response rates were ~40%. Currently, there is no FDA-approved test to detect MSI status. MSI-H tumors share histopathological characteristics, such as high lymphocytic infiltration and high tumor mutation burden. Specifically, these tumors have a high number of insertion-deletion (indel) mutations, which are known to be highly immunogenic leading to an abundance of neoantigens. It follows from our finding that MSI-H tumors having high indel rates will likely be highly responsive to immunotherapy with antibodies targeting immune checkpoint molecules such as PD-1, PD-L1, or PD-L2. Therefore, in another possible embodiment, a method for analyzing MSI loci according to the invention is provided, which comprises a step of using the information obtained about the number of the homopolymeric repeats, in order to decide about subjecting the person from whom the biological sample was obtained to immunotherapy. In possible embodiments, the method may comprise a step of using the information obtained about the number of the homopolymeric repeats to deduce tumor mutation load or tumor indel load. In a preferred embodiments of said method, the deduced tumor mutation load or the tumor indel load is provided as an estimation of the total number of mutations, or is provided as a score. In a particular embodiment, the methods of the invention may comprise the step of using the information obtained about the number of the homopolymeric repeats, or the tumor mutation load, or the tumor indel load, or the estimation of the total number of mutations, or the score, in order to decide about subjecting the person from whom the biological sample was obtained to immunotherapy. As explained above, in preferred embodiments of such methods, the immunotherapy comprises a treatment with an immune checkpoint factor-targeting antibody, said antibody most preferably being an antibody specific to any of the following targets: PD-1, PD-L1, or PD-L2. In a further aspect, our data also suggests that the high-neoantigen-bearing tumors would also be responsive to approaches specifically targeting the generated neoantigens by means of chimeric antigen T cell or therapeutic vaccine therapies. Possible embodiments of the methods of the invention implementing said means can thus also be envisaged. These and other uses of the present invention in diagnosis, prognosis, and clinical follow-up of subjects will further be easily derivable for the skilled in the art.

EXAMPLES

1. Detection of Microsatellite Instability (MSI) in Cancer Samples with a Novel Set of Highly Sensitive Markers A minimal set of 4 markers is not trivial to derive from any given set of markers. For example, the described by Zhao et al, 2014, eLife, Sequenom analysis of 18 MSI-H samples using a panel of 59 markers revealed that a marker is on average called mutant in 44.26% of the samples. While this large panel of markers is highly performant in detecting MSI status, derived therefrom random sets of 4 selected markers show a much worse theoretical performance compared to the proposed herein core set comprising ACRV2A, DIDO1, MRE11, SULF2. Such randomly selected panels are additionally prone to suffer from the drawback that they may contain markers displaying ethnicity dependent differences in the homopolymer region, such as it was e.g. seen in the marker TMEM65 for Caribbean subpopulations. Such differences make it extremely difficult to design a robust and performant low-number marker panel as they may compromise the correct interpretation of MSI driven changes. The latter becomes especially relevant when calling a low amount of variable markers and/or when lacking an appropriate control, which is commonly seen e.g. with the classical Bethesda set of MSI biomarkers having a broad individual variation range and multiple variant alleles, especially in African populations (Buhard et al., 2006).

MSI Profiling in CRC, Gastric Cancer and Endometrium Cancer

The status of 7 microsatellite markers (BTBD7, RYR3, SEC31A, ACVR2A, DIDO1, MRE11 and SULF2) was profiled in 128 MSI-H colorectal cancer samples. Several clinical sites and different ethnic groups were included to assess robustness of marker selection. In addition, the status of the 7 markers was checked in 15 MSI-H gastric cancer samples and 19 MSI-H endometrium cancer samples. Repeat length was determined on FFPE DNA by PCR and followed by amplification product characterization with molecular beacons.

Materials and Methods

Samples. In total 128 human MSI-H CRC FFPE samples were obtained from different sources including Cambridge University, Instituto Portugues de Oncologia do Porto, Cureline, Boca Biolistics, Trans-Hit, Geneticist inc, Righshospitalet, Origene, and Asterand. 15 human MSI-H gastric samples were obtained from Cureline and Trans-Hit and 19 human MSI-H endometrium samples were obtained from IDIBELL.

Sample processing. Each of the MSI-H FFPE samples was inserted into a proprietary to Biocartis Idylla™ fluidic cartridge. The cartridges were closed and loaded onto the Idylla™ platform for automated PCR-based genetic analyses, after which a fully-automated sample processing was initiated. Briefly, DNA was released from the FFPE samples according to the Biocartis FFPE liquefaction protocol, and then was pumped into the PCR compartments of the cartridges in accordance with a standard Idylla™ protocol.

PCR. The PCR compartments of the cartridge were loaded to contain the following PCR mixes per primer pair or primer pair duplex, as indicated below:

| | | Final Concentration in PCR | |
|---|---|---|---|
| | | Conc | Units |
| BTBD7 | | | |
| Fw primer | | 0.2 | µM |
| Rev primer | | 1 | µM |
| Molecular Beacon | | 0.2 | µM |
| dNTPs | | 1.1 | mM |
| Trehalose | | 24 | mM |
| Enzyme: Veraseq Ultra | | 5 | U |
| Tris pH 8 | | 100 | mM |
| MgCl2 | | 3 | mM |
| KCl | | 37.5 | mM |
| (NH4)2SO4 | | 20 | mM |
| ProClin300 | | 0.05 | % |
| RYR3 | | | |
| Fw primer | | 0.2 | µM |
| Rev primer | | 1 | µM |
| Molecular Beacon | | 0.2 | µM |
| dNTPs | | 1 | mM |
| Trehalose | | 24 | mM |
| Enzyme: Veraseq Ultra | | 5.0 | U |
| Tris pH 8 | | 100 | mM |
| MgCl2 | | 3 | mM |
| KCl | | 37.5 | mM |
| (NH4)2SO4 | | 20 | mM |
| ProClin300 | | 0.05 | % |
| ACVR2A/SEC31A | | | |
| ACVR2A | Fw primer | 0.2 | µM |
| | Rev primer | 1 | µM |
| | Molecular Beacon | 0.2 | µM |
| SEC31A | Fw primer | 0.2 | µM |
| | Rev primer | 1 | µM |
| | Molecular Beacon | 0.2 | µM |
| | dNTPs | 1.05 | mM |
| | Trehalose | 24 | mM |
| | Enzyme: Veraseq Ultra | 5.0 | U |
| | Tris pH 8 | 100 | mM |
| | MgCl2 | 3 | mM |
| | KCl | 37.5 | mM |
| | (NH4)2SO4 | 20 | mM |
| | ProClin300 | 0.05 | % |
| DIDO1/MRE11 | | | |
| DIDO1 | Fw primer | 0.2 | µM |
| | Rev primer | 3 | µM |
| | Molecular Beacon | 0.2 | µM |
| MRE11 | Fw primer | 0.2 | µM |
| | Rev primer | 3 | µM |
| | Molecular Beacon | 0.2 | µM |
| | dNTPs | 0.9 | mM |
| | Trehalose | 24 | mM |
| | Enzyme: Veraseq Ultra | 5.0 | U |
| | Tris pH 8 | 100 | mM |
| | MgCl2 | 3 | mM |
| | KCl | 37.5 | mM |
| | (NH4)2SO4 | 20 | mM |
| | ProClin300 | 0.05 | % |
| SULF2 | | | |
| Fw primer | | 0.2 | µM |
| Rev primer | | 1 | µM |
| Molecular Beacon | | 0.2 | µM |
| dNTPs | | 1 | mM |
| Trehalose | | 24 | mM |
| Enzyme: Veraseq Ultra | | 5.0 | U |
| Tris pH 8 | | 100 | mM |
| MgCl2 | | 3 | mM |
| KCl | | 37.5 | mM |
| (NH4)2SO4 | | 20 | mM |
| ProClin300 | | 0.05 | % |

The sequences of the primer pairs and probes per marker were as follows:

| marker | oligo | sequence | SEQ ID NO. |
|---|---|---|---|
| DIDO1 | fwd | TAGCGTGTGAATCGGACAT | SEQ ID NO.: 1 |
| | rev | TTGACTGGGCAGATAGGGGA | SEQ ID NO.: 2 |
| | probe | CGCACGACATGGAAAAAAAAAATCCGTGCGTAAA | SEQ ID NO.: 15 |
| MRE11 | fwd | ATAGTTCACCCATGGAAACC | SEQ ID NO.: 3 |
| | rev | GGAGGAGAATCTTAGGGAAA | SEQ ID NO.: 4 |
| | probe | CGTCGAACCTTAAAAAAAAAAGTTACCGACGAA | SEQ ID NO.: 16 |
| BTBD7 | fwd | ACTGGACTCCCGCTGG | SEQ ID NO.: 5 |
| | rev | CGCTCAGCCTCCATAAATC | SEQ ID NO.: 6 |
| | probe | CGCACGACTTATTAAAAAAAAATGACAGTGCGTAAA | SEQ ID NO.: 17 |
| SULF2 | fwd | CAACTTCATTTCTTTTCAGTACCTT | SEQ ID NO.: 7 |
| | rev | CTGTCCAGATACCATTTCTC | SEQ ID NO.: 8 |
| | probe | CGTCGGTACCTTAAAAAAAAACATCACGACGAA | SEQ ID NO.: 18 |

-continued

| marker | oligo | sequence | SEQ ID NO. |
|---|---|---|---|
| ACVR2A | fwd | AGCATCCATCTCTTGAAGACAT | SEQ ID NO.: 9 |
| | rev | GCATGTTTCTGCCAATAATCTCT | SEQ ID NO.: 10 |
| | probe | GTGCATAAAAAAAGAGCACTAAA | SEQ ID NO.: 19 |
| SEC31A | fwd | CAACTTCAGCAGGCTGT | SEQ ID NO.: 11 |
| | rev | AGTCTGAGAAGCATCAATTTT | SEQ ID NO.: 12 |
| | probe | CGCACTTGCCAAAAAAAATTGATGGTGCGTAAA | SEQ ID NO.: 20 |
| RYR3 | fwd | CATTTTCTAAATGCCTCCCTTAAA | SEQ ID NO.: 13 |
| | rev | GTCCATTAGGCACAAAAAG | SEQ ID NO.: 14 |
| | probe | CGTCGCCCTTAAAAAAAAACTGCCGACGAA | SEQ ID NO.: 21 |

The PCR conditions were as follows:

| | Temperature (° C.) | Time (min:sec) | # Cycles |
|---|---|---|---|
| Initial Denaturation | 92 | 00:30 | |
| Amplification | 92 | 00:10 | 60 |
| | 60 | 00:10 | |
| Denaturation | 92 | 02:00 | |
| Melting curve | from 40 to 76.6° C., increment 0.3° C. | 00:05 | |

Amplicon melting. The PCR products were denatured in the cartridges for 2 min at 92° Next, a melting curve fluorescence data was collected by heating the mixture from 40° C. to 76.6° C. in steps of 0.3° C. (12 s per cycle) and at the same time monitoring the fluorescence signals after every 0.3° C. increase.

Post-processing. In the first step in data analysis, the raw fluorescence measurement values of the melting curve are retrieved from the Idylla™ instrument. In the following step only the first 64 cycles are retained from the vector of measurement values. This subset is named the "region of interest" or ROI because the most important changes in signal are observed within this window. In later cycles the melting of beacons is mostly observed. The next step in the post-processing algorithm is the application of a discrete wavelet transform (DWT) to the measurement vector (ROI). Wavelets are especially well suited for the analysis of a melting curves because this is low frequency phenomenon that occurs in a specific temperature zone. Wavelets are capable of performing a time and frequency analysis at the same time. This means that they can interpret both what is happening in terms of low frequency changes and when this is happening. As such wavelets compactly summarize the melting curve process. In this specific case, the DB8 wavelet is used and the third level coefficients are retained. After this transform, both the scale and the wavelet coefficients are retained, resulting in two sets of 8 coefficients. One set of 16 wavelet coefficients is calculated for each marker present in the assay. This set of wavelet coefficients per marker is named the post-processing results for each marker.

Decision tree. The second step of the data analysis of the melting curve data is called the decision tree. In this step, a pattern recognition algorithm is applied in order to classify valid samples based on the post-processing results. To this end, a classification algorithm being a neural network is applied to the post-processing results of each marker. This network has been trained with labeled data for which the input genotype is known. In the case of reference data, this labelling is based on the input genotype that was reported. For clinical data this labelling is obtained from the visual scoring of the melting profiles by melting curve experts.

Through the iterative optimization of the weights within the neural network, the algorithm can learn to distinguish between a wild type (WT) and a mutant curve. The algorithm gives a probability score as output for each marker gene that reflects the certainty of the decision (1 for mutant and 0 for WT). A sample is scored as MSI-H if at least two markers have a probability score higher than 0.5.

Results

1. MSI Profiling in CRC

First analysis. A core set of four markers including ACVR2A, DIDO1, MRE11, and SULF2 was assessed in their ability to recover MSI-H positive samples out of the pool of 128 MSI-H samples. A sample is scored positive when the decision tree of the post-processed melting curve data results in at least two markers as being detected as comprising an indel. Using this core set of four markers, 96% of the samples could be identified as MSI-H. Because the minimal acceptable performance has been defined to recover at least 95% of the samples, the selection made above has been accepted as the core set of MSI markers.

| # Markers | Markers | #MSI | % MSI |
|---|---|---|---|
| 4 Core | ACVR2A, DIDO1, MRE11, SULF2 | 123 | 96% |

To create a further assessment of the performance of these markers, all possible permutations of 3 markers from the core panel of 4 were subjected to the same performance analysis. Results indicate that performance is worse for every possible subselection, ranging from 83% to 93%. In order to supply more robustness to the assay across cancer types a design with at least four markers is preferred.

| # Markers | Markers | #MSI | % MSI |
|---|---|---|---|
| sub 3 | ACVR2A, DIDO1, SULF2 | 119 | 93% |
| sub 3 | ACVR2A, DIDO1, MRE11 | 118 | 92% |
| sub 3 | ACVR2A, MRE11, SULF2 | 109 | 85% |
| sub 3 | DIDO1, MRE11, SULF2 | 106 | 83% |

Second analysis. By adding an additional marker (BTBD7) to the core set of four markers, one more sample can be scored as MSI-H, accounting for 97% of correctly scored samples and thus making the panel more efficient in defining the MSI status.

| # Markers | Markers | #MSI | % MSI |
|---|---|---|---|
| 4 Core + BTBD7 | ACVR2A, DIDO1, MRE11, SULF2, BTBD7 | 124 | 97% |

Third analysis. By adding an additional marker (SEC31A) to the five marker set, all samples in the tested limited sample set can be scored as MSI-H, which provides an even further improvement.

| # Markers | Markers | #MSI | % MSI |
|---|---|---|---|
| 4 Core + BTBD7 + SEC31A | ACVR2A, DIDO1, MRE11, SULF2, BTBD7, SEC31A | 128 | 100% |

Fourth analysis. By adding a further marker (RYR3) to the set of six markers, naturally, still all samples are scored as MSI-H. Although not immediately visible from the present data, in theory, addition of a $7^{th}$ marker is likely to still increase the performance of the assay in case larger sample sets are analyzed. In theory, given the observed frequencies of these markers being mutated in MSI-H samples, for 7 markers the false negative rate is predicted to be as low as ~1/1900, which for larger sample sets may become relevant.

| # Markers | Markers | #MSI | % MSI |
|---|---|---|---|
| 4 Core + BTBD7 + SEC31A + RYR3 | ACVR2A, DIDO1, MRE11, SULF2, BTBD7, SEC31A, RYR3 | 128 | 100% |

The results of the CRC sample analysis are shown in FIG. 1.

2. MSI Profiling in Gastric Cancer and Endometrium Cancer

First analysis. The core set of the four best performing in CRC markers (ACVR2A, DIDO1, MRE11, and SULF2) was then also assessed in a pool of 34 cancer samples including 15 gastric cancer samples and 19 endometrium (EN) cancer samples.

| # Markers | Markers | #MSI | % MSI |
|---|---|---|---|
| 4 Core | ACVR2A, DIDO1, MRE11, SULF2 | 32 | 94% |

The results suggest that the homopolymeric repeat in the ACVR2A is a much more potent marker in CRC than in other cancer types. However, despite a very small sample pool the results of the core set in gastric and EN cancer come very close to the acceptable threshold of 95%, which is a good indicator that in a larger sample pool the presented herein core 4 marker set can generally be applied to other MMR-deficient or microsatellite-unstable tumor types and not only CRC. In order to have a better view on the core panel performance, more samples would have to be profiled.

Second analysis. By adding an additional marker (BTBD7) to the core set of four markers, one more sample can be scored as MSI-H, which in this small sample set already brings the performance of such five marker panel to a highly satisfactory value of 97% of correctly scored samples.

| # Markers | Markers | #MSI | % MSI |
|---|---|---|---|
| 4 Core + BTBD7 | ACVR2A, DIDO1, MRE11, SULF2, BTBD7 | 33 | 97% |

Third analysis. By adding an additional marker (SEC31A) to the five marker set, all samples can be scored as MSI-H.

| # Markers | Markers | #MSI | % MSI |
|---|---|---|---|
| 4 Core + BTBD7 + SEC31A | ACVR2A, DIDO1, MRE11, SULF2, BTBD7, SEC31A | 34 | 100% |

3. Automated MSI Profiling of 7 Markers by Means of the Idylla™ MSI Test

Background: Detection of microsatellite instability (MSI) has been recommended for all patients with colorectal cancer (CRC). Current clinical reference methods are immunohistochemical staining of mismatch repair proteins and/or PCR analysis of frequently mutated short tandem repeat regions of DNA. The Idylla™ MSI Test is developed using a new set of short homopolymers, selected from whole exome sequence data in an unbiased way (Zhao et al. 2014; eLife), capable of faster detection with greater specificity and selectivity compared to current methods.

Methods: Prototype Idylla™ MSI Test cartridges were developed up to a finalized design.

Repeat length of a novel set of 7 biomarkers was determined on 348 formalin-fixed and paraffin-embedded (FFPE) CRC samples using these prototype tests which allow a complete automated workflow including sample preparation, DNA amplification followed by melting curve analysis and automated interpretation. Several clinical sites and different ethnic groups of the patient's samples were included to assess robustness of marker selection. All samples were additionally screened with a reference methodology for MSI detection (Promega MSI analysis system).

Results: One hundred twenty-seven (36.5%) and 116 (33.3%) samples were classified as MSI-high (MSI-H) and 209 (60.1%) and 220 (57.3%) samples were classified as microsatellite stable (MSS) by Idylla™ and Promega respectively, while 12 samples (3.4%) could not be classified by either methodology. Concordance analysis revealed an overall agreement of 96.1% (93.4%-97.7% 95% CI). 14 cases were MSI-H by Idylla™ but MSS (11) or invalid (3) by Promega; with a median of 3/7 positive markers on Idylla™.

Conclusions: This study validated the novel MSI biomarkers to discriminate MSI-H from MSS status on a large and diverse set of CRC samples. It also demonstrated the possibility of a fully automated analysis for MSI testing. The prototype Idylla™ MSI Test is compatible with the fully integrated Idylla™ platform providing accurate and reliable results within 150 minutes from just one FFPE tumour section (no reference sample required).

General Conclusions

The presented herein panel of only four core markers including the homopolymeric repeats in the ACVR2A, DIDO1, MRE11, and SULF2 genes, shows an extremely good performance in CRC samples. It also shows a very good performance in gastric and endometrial cancer samples, even despite the fact we had access and could profile only very few of them. Profiling more MSI-H samples of origin other than CRC will likely corroborate the applicability of the minimal core panel of two markers to a broader spectrum of cancers. Currently, it appears that the homopolymer in the ACVR2A gene is a particularly performant and quite specific MSI marker for CRC. Consequently, in other cancer types, as alternative embodiments of the invention, other minimal core panels could possibly be proposed and tested. From the presented herein preliminary data it appears that the following three core 4-marker panels could be proposed: (1) DIDO1, SULF2, BTBD7 and SEC31A; (2) DIDO1, SULF2, BTBD7 and ACVR2A; and (3) DIDO1, SULF2, SEC31A, and RYR3. Regardless of the MMR-deficient sample types, a core 5-marker panel comprising ACVR2A, DIDO1, MRE11, SULF2, and BTBD7 was shown to be generally suitable for diagnosing samples of different origins and therefore constitutes a particularly attractive embodiment of the present invention.

2. A Novel Set of 7 Homopolymer Indels for Detection of MSI is Associated with Tumor Mutation Burden and Total Indel Load in Endometrial and Colorectal Cancers Background: Immune checkpoint blockade was recently approved for the treatment of unresectable or metastatic, microsatellite-instability-high (MSI-H) tumors regardless of site or histology. Observed response rates were ~40%. Currently, there is no FDA-approved test to detect MSI status. MSI-H tumors share histopathological characteristics, such as high lymphocytic infiltration and high tumor mutation burden. Specifically, these tumors have a high number of insertion-deletion (indel) mutations, which are, as opposed to single nucleotide variants, known to cause frameshifts and therefore leads to an abundance of neoantigens that are highly immunogenic. High indel rates in MSI-H tumors may therefore predict response to anti-PD1 therapy.

Methods. We selected MSI and MSS tumors for which whole-exome-sequencing data were available from our previous report (Zhao et al., eLife 2014). These included 11 MSI samples from endometrial cancer, 22 MSI samples from colorectal cancer, and 89 MSS samples. Then we determined mutational load stratified for substitutions and indels based on the whole-exome-sequencing data. Seven markers as described herein were amplified and paired-end amplicon-based sequencing was performed on Illumina HiSeq 4000. Amplicons were sequenced at a minimal coverage of 5.000× and at an average coverage of 87.000×. MSS samples were used to calculate average percentage of reads with deletions. A marker was considered positive when the percentage of mutated reads was larger than 6 SDs (corresponding to a P-value <$1.0e^{-5}$). Several of the markers gave high mutant background rates due to polymerase slippage in the homopolymer region. This ranged between 6.6% (for ACVR2A) to 36.0% (for BTBD7).

Figure 5A:
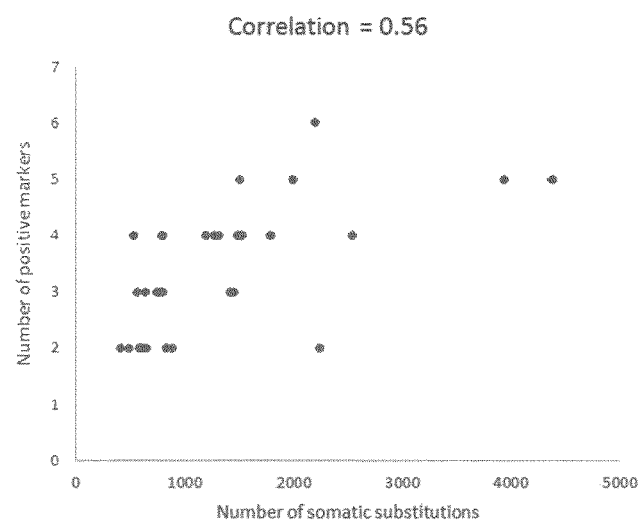
FIG. 5A: Correlation plot between the number of mutant microsatellite markers from 1 to 6 (BTBD7, RYR3, SEC31A, ACVR2A, DIDO1 and MRE11) with mutation load in MSI samples measured by (A) number of somatic substitutions (while correcting with indels, number of substitutions and number of mutant markers are correlated with p value=1.92e-07) or (B) number of somatic indels (while correcting with substitutions, number of indels and number of mutant markers are correlated with p value=7.1e-07) (C) Correlation between somatic substitutions and indels in MSI tumors, showing high correlation between somatic substitutions and indels in MSI-H samples. The correlation is consistent for both EM MSI tumors and CRC MSI tumors, but not in MSS tumors.
Figure 5A:
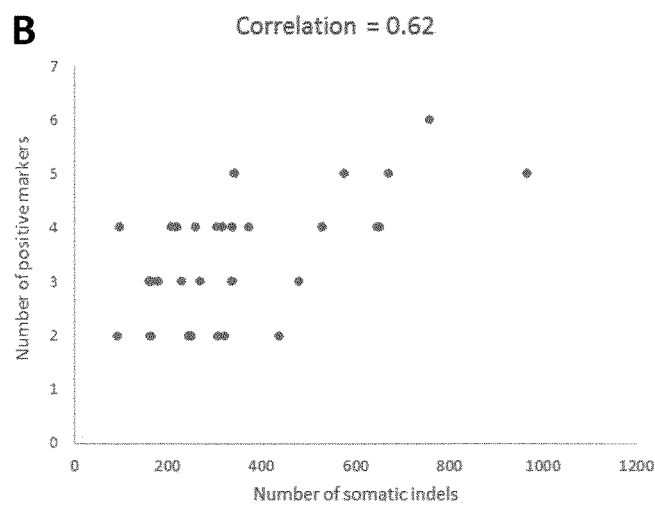
Figure 5A:
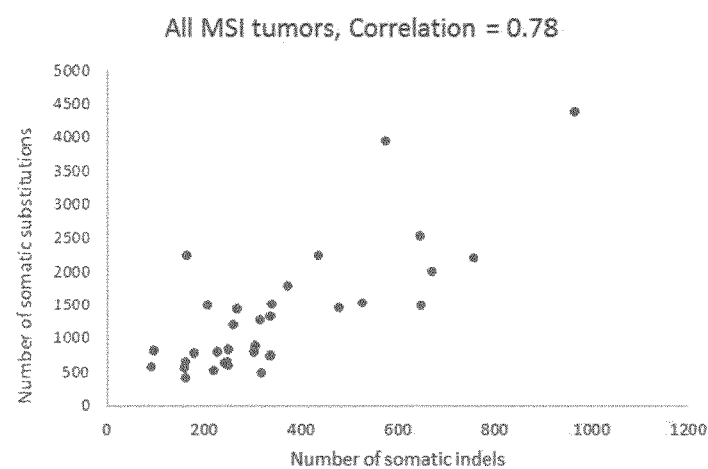
Figure 5B:
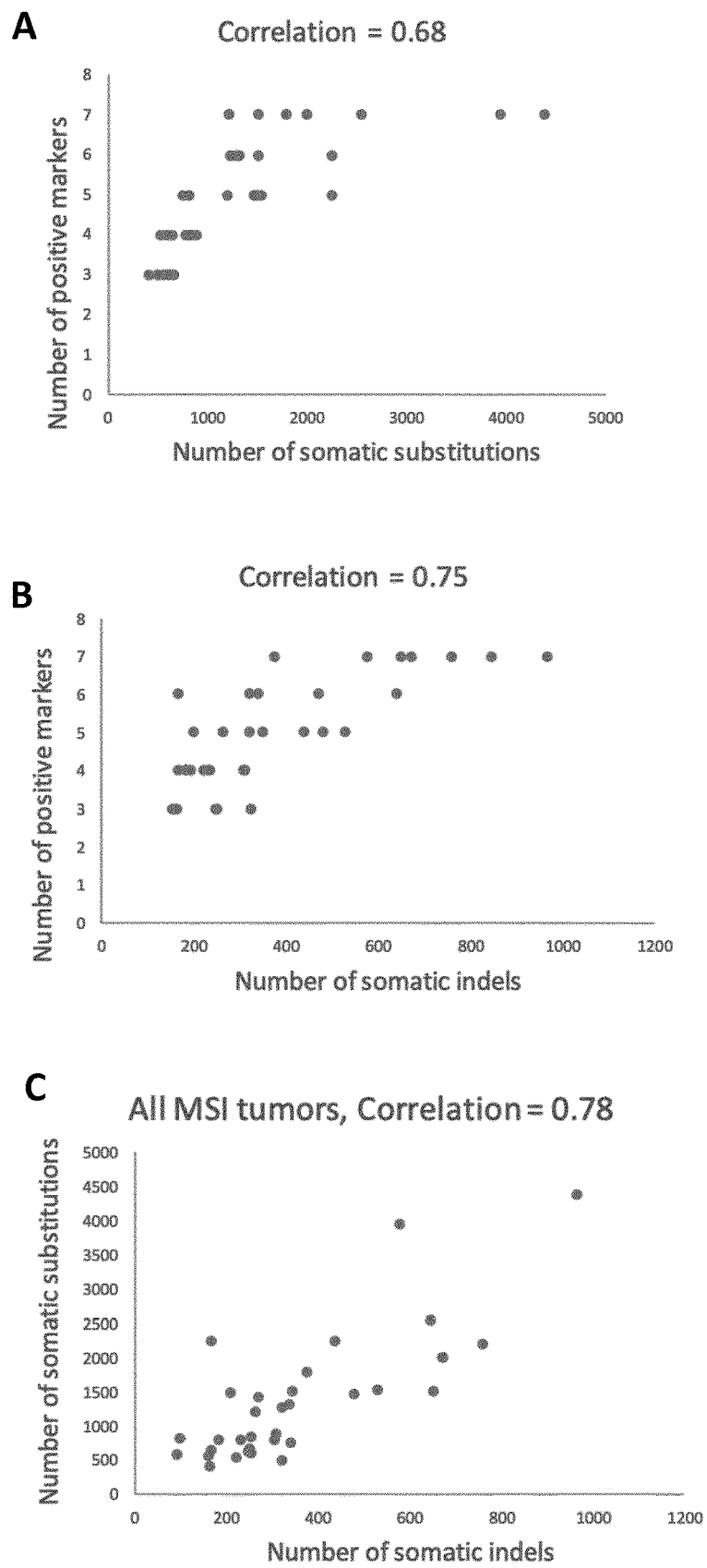
FIG. 5B: Correlation plots between number of mutant microsatellite markers and mutation load as shown in FIG. 5A above but completed with data for one more marker (SULF2). In (A), showing the correlation with the number of somatic substitutions, the addition of one more marker changed the p value to 6.5e-05). In (B), showing the correlation with the number of somatic indels, the addition of one more marker changed the pvalue to 2e-16. In (C), showing the correlation between somatic substitutions and indels, it can be seen that addition of one more marker further improves the correlation's significance in MSI-H samples.

Results. Nineteen MSI-H tumors were positive for at least 2 out of 6 initially screened due to technical difficulty (shown in FIG. 5A), then complete 7 (shown in FIG. 5B) indels, while MSS tumors were positive for none of them. Additionally, we correlated the number of positive indels in all available MSI-H tumors (n=19+14) with mutation load. This revealed a positive correlation for both non-synonymous and indel mutation load (values for complete 7 indels correlated: r=0.68 p<$6.5e^{-05}$ and r=0.75 p<$2e^{-16}$, respectively). Per additional indel marker that was positive, we observed an increase in indel mutation rate of 119 indels, starting with a median of ~250 indels as of 3 markers positive. The results are shown in accompanying FIGS. 3-6.

Conclusion. A selection of 7 indels reliably detects MSI-H in endometrial and colorectal cancer, while the number of positive indels serves as a proxy for tumor mutation load as well as tumor total indel load, and may thus be used as a test for tumor neoantigen load predictive of response to anti-PD-1 therapy in MSI-H tumors. These 7 markers will be available as a fully automated Idylla™ MSI test to detect MSI status and could be used as a companion diagnostic to predict immunotherapy outcome in MSI-H tumors.

3. Overview of CRC Tumor Staging Related to Valid, Invalid, Error and Discordant Results for Idylla™ MSI Test and IHC Analysis Materials. The study was performed on 330 residual FFPE samples obtained from routine diagnostics by two University Hospitals, University Hospital Aarhus (site 1) and University Hospital Antwerp (site 2). The samples originated from CRC patients and were representative for all stages of CRC, including stage I. The MSI IHC data were made available by both study sites and based on standard of care (SoC) IHC test results on historical FFPE sections (retrospective pathological data). Both sites performed MSI testing using an Idylla™ MSI Test comprising the 7 described markers herein. The tests were performed at the premises of both sites on a set of 150 and 180 samples, respectively. For informational purposes, concordance between the Idylla™ MSI Test and historical MSI immunohistochemical (IHC) data was performed. Of the 330 samples, staging information was not available for 16 samples (cf. table in FIG. 7) and was based on the data available in the pathological report. For several cases, Tumor, Nodes and Metastases (TNM) staging (according to $7^{th}$ edition of the American Joint Committee on Cancer, Colon and Rectum Cancer Staging) has been derived from T and N parameters only due to limited source per pathological report. In the current study population, 6,7% (N=22), 19.4% (N=64), 43.3% (N=143) and 25.8% (N=85) were stage I, stage II, stage III and stage IV respectively as shown in the first column of FIG. 7.

Methods. The Idylla™ MSI Test was performed on the FFPE samples in an automated manner using a proprietary to Biocartis cartridge-based and platform Idylla™. The FFPE samples were inserted to individual cartridges comprising reagents as described above, after which the cartridges were operated and analysed by the automated platform in accordance with the described above protocols. Then the results obtained for the Idylla™ MSI Test were juxtaposed to the MSI status assessment of the FFPE samples as was evaluated by IHC. The invalid result for two FFPE samples was confirmed by cross-testing with a Bethesda-panel-based Promega MSI Analysis System v 1.2 in accordance with the manufacturer's validated protocol.

Figures 6, 7:
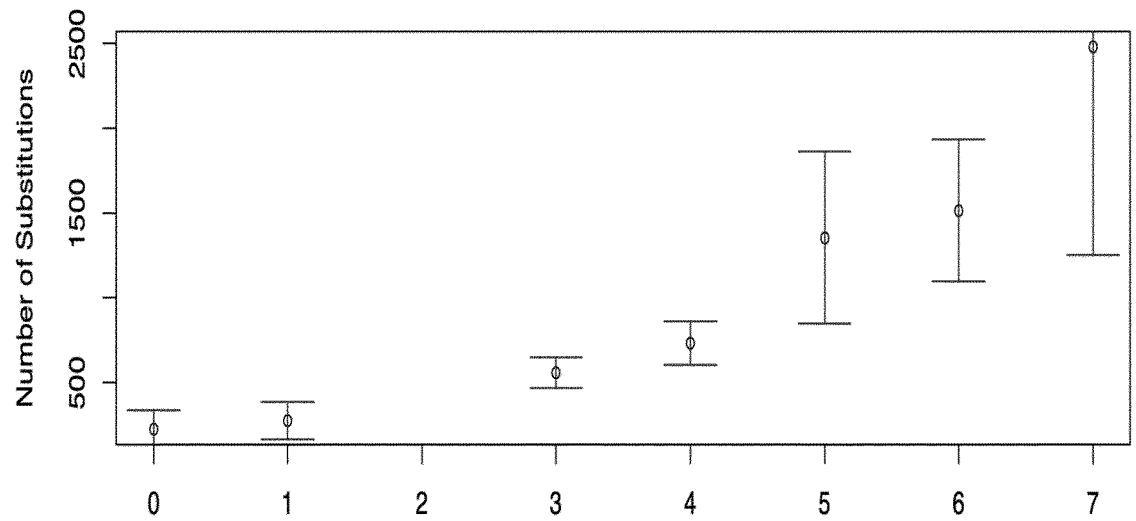
FIG. 6: Number of positive markers as a predictor for tumor mutational burden (TMB). On average, 348 more substitutions and 119 more indels were observed with an increase of one positive marker (data shown for 7 markers as presented in FIG. 5B).
FIG. 7: Overview of CRC tumor staging related to valid, invalid, error and discordant results for the MSI testing method of the invention as implemented on Biocartis Idylla platform as compared to IHC analysis.

Results. The comparison between Idylla™ MSI Test and historical immunohistochemistry (IHC) MSI data was made available for informational purposes only, and is shown in FIG. 7. The results show that only two of the 330 total sample results were scored as invalid in the Idylla™ MSI Test and that the test is robust as no errors were encountered throughout the 330 performed runs. The test invalidity for the two samples likely was caused by their poor quality, which was confirmed by the Promega MSI Analysis System v 1.2 that also failed to analyse said samples (data not shown). The results generally show good concordance between Idylla™ MSI Test and the IHC results. Importantly, in line with the IHC results, the Idylla™ MSI Test also correctly identified the MSI-H phenotype in two samples of stage I CRC. This demonstrates that to identify early stage MSI-H tumours one does not only have to test the presence of lesions in the MMR pathway on the protein level, but can also detect the microsatellite instability signature at DNA level.

Conclusion. The results confirmed the robustness of the MSI analysis methods according to the invention and provided the first to our knowledge clinical proof that a molecular MSI signature test can correctly identify MSI-H status in stage I CRC. This indicates that the test will most likely also be able to correctly identify MSI-H status also in other stage I cancer types.

Definitions

As used herein, the term "biological sample", or simply "sample", is intended to include a variety of biological sources that contain nucleic acid and/or cellular material, irrespective whether it is freshly obtained from an organism (i.e. fresh tissue sample) or preserved by any method known in the art (e.g. an frozen or an FFPE sample). Examples of biological samples include: cultures of cells such as mammalian cells but also of eukaryotic microorganisms, body fluids, body fluid precipitates, lavage specimen, fine needle aspirates, biopsy samples, tissue samples, cancer cells, other types of cells obtained from a patient, cells from a tissue or in vitro cultured cells from an individual being tested and/or treated for disease or infection, or forensic samples. Non-limiting examples of body fluid samples include whole blood, bone marrow, cerebrospinal fluid (CSF), peritoneal fluid, pleural fluid, lymph fluid, serum, plasma, urine, chyle, stool, ejaculate, sputum, nipple aspirate, saliva, swabs specimen, wash or lavage fluid and/or brush specimens.

The term "nucleic acid" and its equivalent "polynucleotide", as used herein, refer to a polymer of ribonucleotides or deoxyribonucleotides bound together by phosphodiester linkages between the nucleotide monomers. (Deoxy)nucleotides are phosphorylated forms of (deoxy)nucleosides, which most commonly include adenosine, guanosine, cytidine, thymidine, or uridine. These nucleosides consist of a pentose sugar, being ribose or deoxyribose, and a nitrogenous base ("nucleobase", or simply, "base") being either adenine, guanine (that are purines), cytosine, thymine, or uracil (being pyrimidines). The sequence at which these bases (or their nucleosides, or the nucleotides of the latter) follow in a nucleic acid strand is termed "nucleic acid sequence" and is conventionally given in a so called 5'-end to 3'-end direction referring to chemical orientation of the nucleic acid stand. The "5'" originates from the reference to the 5' carbon of the first (deoxy)ribose ring from which the reading of the nucleic acid sequence begins, and the "3'" originates from the 3' carbon of the last (deoxy)ribose ring on which the reading of the nucleic acids sequence ends. A nucleic acid sequences can e.g. be ATATGCC, which is to be interpreted herein as referring to 5'-ATATGCC-3' nucleic acid sequence. Under the same convention, the latter sequence will be complementary to the sequence 5'-GGCATAT-3', or simply GGCATAT. A nucleic acid sequence can be a homopolymeric repeat sequence i.e. a sequence made of a certain number of consecutive nucleotides that comprise the same nitrogenous base, which are also termed herein "homonucleotides". For example, a term "homopolymeric repeat comprising 8 consecutive adenines" is to be construed as referring to at least a part of a nucleic acid, said part being made of a track comprising 8 consecutive nucleotides, wherein each of said nucleotides comprises an adenine as the nitrogenous base. Such sequence would be designated as 5'-AAAAAAAA-3' (or, simply AAAAAAAA), while its complementary sequence would be 5'-TTTTTTTT-3' (or TTTTTTTT). The terms "mutated form of a homopolymeric repeat" or "mutated forms thereof" are to be construed herein as referring to MSI variants of a given homopolymeric repeat that comprise an insertion or a deletion (i.e. an "indel") of at least one homonucleotide. For example, a mutated form of the homopolymeric repeat comprising 8 consecutive adenines, would be a homopolymeric repeat comprising 7 consecutive adenines, or a homopolymeric repeat comprising 9 consecutive adenines. Nucleic acids include but are not limited to DNA and RNA, including genomic DNA, mitochondrial or meDNA, cDNA, mRNA, rRNA, tRNA, hnRNA, microRNA, IncRNA, siRNA, and various modified versions thereof. Nucleic acids can most commonly be obtained from natural sources like biological samples obtained from different types of organisms. On the other hand, nucleic acids can also be synthesized, recombined, or otherwise produced in any of the known human-devised methods (e.g. PCR).

The term "quantitative PCR" or simply "qPCR" is herein given the definition of a laboratory technique based on the polymerase chain reaction (PCR), which is used to amplify and simultaneously detect or quantify a targeted DNA molecule. In contrast to standard PCR where the product of the reaction is detected at its end, i.e. after thermocycling has finished, the key feature of qPCR is that the DNA product is being detected during thermocycling as the reaction progresses in "real time"; hence, the alternative name of qPCR "real-time PCR". There currently exist many different types of qPCRs. For example, when starting with a reverse transcription (RT) step, qPCR can be used to quantify numbers of messenger RNAs and is then called a reverse transcriptase qPCR or an RT-qPCR. As used herein the terms "quantitative PCR" or simply "qPCR" will be employed with preference over the term "real-time PCR" or "RT-PCR" in order to avoid confusion with reverse transcription PCR, also frequently abbreviated as RT-PCR. Most qPCRs use one of the two most common methods for detecting the product amplification in real-time: (a) intercalation of non-specific fluorescent dyes with any double-stranded DNA, or (2) sequence-specific DNA probes consisting of oligonucleotides that are labelled with a fluorescent reporter which permits detection only after hybridization of the probe with its complementary target sequence. The fluorescent signals generated during thermocycling are detected by an appropriate optical detection system and tracked from the moment they pass the background threshold till the reaction reaches plateau. The copy number of the target sequences can be estimated using either relative or absolute quantification strategy, typically by analyzing the shape of the obtained amplification curve (standard curve strategy) or by determining when the signal rises above some threshold value (often called the Ct value, but sometimes also Cp value or Cq value). In relative quantification, the target nucleic acid levels estimated in a given sample using the Ct or standard curve analysis are expressed as relative to values obtained for the same target in another reference sample, for example, an untreated control sample. Conversely, in absolute quantification the qPCR signal is related to input copy number using a standard curve or can also be calculated according to a more recent digital PCR method. For the moment being, the first strategy is still more prevalent and bases the estimation of the target DNA amount by comparing the obtained values with a previously made standard curve. These and other qPCR quantification strategies are broadly known in the art and their calculation can differ in smaller or greater depending on a given application and a qPCR system.

As used herein, the term "means for performing quantitative PCR" shall be understood as minimum necessary arrangement of reagents and elements for performing a qPCR. They will usually include any reagents allowing detectable in real time PCR thermocycling of a nucleic acid template received from a source of nucleic acid. Such reagents include but depending on the type of qPCR are not limited to a PCR-grade polymerase, at least one primer set a detectable dye or a probe, dNTPs, PCR buffer etc. Further, the "means for performing quantitative PCR" will usually also include any standard known in the art minimal assembly of parts, which usually includes but is not limited to the following: (1) a suitable compartment (further referred to as a "a thermocycling qPCR compartment") where the real time-detectable thermocycling can take place. Such compartments can e.g. be formed by a chamber suitable for amplifying nucleic acids, i.e. made from appropriate material and providing for sufficient internal temperature regulation, and also comprising at least one wall allowing real-time detection of signals generated during such amplification, e.g. a wall transparent to light. Further, (2) means for varying temperature in this chamber or other compartment, as broadly known from various existing thermocycling machines. Then, (3) means for detecting the signals generated during the qPCR thermocycling, like an optical detector coupled to a computer etc. In brief, such minimal assembly will normally include any known in the art system or systems capable of initiating and maintaining the thermocycling reaction in the thermocycling qPCR compartment, adjusting and regulating the temperature to ensure stable thermocycling conditions therein etc. Further, it will also include any appropriate detection device or devices, means for data processing (e.g. a computer alternatively connected to a database), and output systems allowing to read and monitor the thermocycling of the qPCR reaction in real-time (usu. a computer screen displaying the reaction progress in an appropriate graphic user interface). Additionally, it will also contain as any software packages suitable for operating the machinery and/or displaying and possibly aiding the interpretation of the obtained results.

As used herein, the term "cartridge" is to be understood as a self-contained assembly of chambers and/or channels, which is formed as a single object that can be transferred or moved as one fitting inside or outside of a larger instrument suitable for accepting or connecting to such cartridge. Some parts contained in the cartridge may be firmly connected whereas others may be flexibly connected and movable with respect to other components of the cartridge. Analogously, as used herein the term "fluidic cartridge" shall be understood as a cartridge including at least one chamber or channel suitable for treating, processing, discharging, or analyzing a fluid, preferably a liquid. An example of such cartridge is given in WO2007004103. Advantageously, a fluidic cartridge can be a microfluidic cartridge. In the context of fluidic cartridges the terms "downstream" and "upstream" can be defined as relating to the direction in which fluids flow in such cartridge. Namely, a section of a fluidic path in a cartridge from which a fluid flows towards a second section in the same cartridge is to be interpreted as positioned upstream of the latter. Analogously, the section to which a fluid arrives later is positioned downstream with respect to a section which said fluid passed earlier.

In general, as used herein the terms "fluidic" or sometimes "microfluidic" refers to systems and arrangements dealing with the behavior, control, and manipulation of fluids that are geometrically constrained to a small, typically sub-millimeter-scale in at least one or two dimensions (e.g. width and height or a channel). Such small-volume fluids are moved, mixed, separated or otherwise processed at micro scale requiring small size and low energy consumption. Microfluidic systems include structures such as micro pneumatic systems (pressure sources, liquid pumps, micro valves, etc.) and microfluidic structures for the handling of micro, nano- and picoliter volumes (microfluidic channels, etc.). Exemplary fluidic systems were described in EP1896180, EP1904234, and EP2419705 and can accordingly be applied in certain embodiments of the presented herein invention.

As used herein, the term "DWT" designates discrete wavelet transform; the term "dwt coefficient" designates discrete wavelet transform coefficient. A wavelet transform means a calculation using a program or subroutine on raw data. Thus a set of dwt coefficients is a wavelet transformed set of values. The most relevant dwt coefficients for nucleic acid analyses are those coefficients that capture the significant events of the experiment, for example in case of a melting experiment of a double-stranded nucleic acid molecule the most relevant dwt coefficients can be peaks or peak shifts in the raw data melting curves.

As used herein, the terms melting curve raw data, raw data melting curve and raw melting curve data are equivalent and used interchangeably. They designate identifiers obtained following nucleic acid dissociation or association experiments.

The invention claimed is:

1. A method comprising:
   (a) performing an amplification reaction on a set of target nucleic acid regions from a biological sample from a subject,
   wherein the target nucleic acid regions, as mapped to the GRCh38/hg38 human reference genome ("reference genome"), consist of:
   human DIDO1 gene starting at position chr20:62,905,340 and encompassing a DIDO1 homopolymeric repeat region, the homopolymeric repeat region comprising 11 consecutive adenines in the reference genome;
   (ii) human MRE11 gene and starting at position chr11:94,479,765, and encompassing a MRE11 homopolymeric repeat region, the homopolymeric repeat region comprising 11 consecutive adenines in the reference genome;
   (iii) human SULF2 gene and starting at position chr20:47,657,577 and encompassing a SULF2 homopolymeric repeat region, the homopolymeric repeat region comprising 10 consecutive adenines in the reference genome;
   (iv) human ACVR2A gene and starting at position chr2:147,926,117 and encompassing an ACVR2A homopolymeric repeat region, the homopolymeric repeat region comprising 8 consecutive adenines in the reference genome;
   (v) human SEC31A gene and starting at position chr4:82,864,412 and encompassing a SEC31A homopolymeric repeat region, the homopolymeric repeat region comprising 9 consecutive thymines in the reference genome;
   (vi) human BTBD7 gene and starting at position chr14:93,241,685 and encompassing a BTBD7 homopolymeric repeat region, the homopolymeric repeat region comprising 10 consecutive adenines in the reference genome;
   (vii) human RYR3 gene and starting at position chr15:33,865,341 and encompassing a RYR3 homopolymeric repeat region, the homopolymeric repeat region comprising 10 consecutive adenines in the reference genome;
   wherein the set of target nucleic acid regions to be amplified is selected from:
   Set I: target nucleic acid regions i-iv;
   Set II: target nucleic acid regions i-iv, and one of target nucleic acid regions v-vii;
   Set III: target nucleic acid regions i-iv; and two of target nucleic acid regions v-vii; and
   Set IV: target nucleic acid regions i-vii;
   wherein if the biological sample comprises a colorectal cancer sample or a suspected colorectal cancer sample, any one of sets i-iv is selected;
   wherein if the biological sample comprises a gastric cancer sample or a suspected gastric cancer sample, or an endometrial cancer sample or a suspected endometrial cancer sample, set iv is selected;
   wherein the step of amplifying comprises, for each target region, at least one amplification primer and at least one molecular beacon probe, each molecular beacon probe designed to hybridize to one of the target regions of the set and comprising a different number of consecutive adenines than the reference target sequence for which it is designed;

(b) generating melting curve data based on the amplification reaction of (a);

(c) applying wavelet transform on the melting curve data generated in (b) to determine the number of consecutive adenines or thymines in the homopolymeric repeats of the target regions in the subject sample.

2. The method of claim 1, wherein at least one amplification primer is selected from the group consisting of SEQ ID NO: 1-4 and 7-10.

3. The method of claim 1, wherein at least one molecular beacon probe is selected from the group consisting of SEQ ID NO: 15, 16, 18, or 19.

4. The method of claim 1, wherein at least one amplification primer is selected from the group consisting of SEQ ID NO: 1-14.

5. The method of claim 1, wherein at least one molecular beacon probe is selected from the group consisting of SEQ ID NO: 15-21.

6. The method of claim 1 further comprising, sequentially or in parallel, performing steps (a)-(c) on a control biological sample comprising nucleic acid derived from HTC116c1.110268743 cell line.

7. The method of claim 1, wherein the step of amplifying comprises at least one duplex amplification of a pair of homopolymeric repeats, or mutated forms thereof, said pair being selected from the following combinations:

duplex amplification of
the homopolymeric repeat comprising 11 consecutive adenines localized to human DIDO1 gene and starting at position chr20:62,905,340
together with
the homopolymeric repeat comprising 11 consecutive adenines localized to human MRE11 gene and starting at position chr11:94,479,765 duplex amplification of
the homopolymeric repeat comprising 8 consecutive adenines localized to human ACVR2A gene and starting at position chr2:147,926,117;
together with
the homopolymeric repeat comprising 9 consecutive thymines localized to human SEC31A gene and starting at position chr4:82,864,412; and duplex amplification of
the homopolymeric repeat comprising 10 consecutive adenines localized to human BTBD7 gene and starting at position chr14:93,241,685;
together with
homopolymeric repeat comprising 10 consecutive adenines localized to human SULF2 gene and starting at position chr20:47,657,577.

8. The method of claim 1, wherein the biological sample from the subject comprises a stage I colorectal tumor sample.

9. The method of claim 1, wherein the method is performed at least in part by an automated system that comprises a console and an instrument compatible with a reusable cartridge.

* * * * *

SEQUENCE LISTING

<160> NUMBER OF SEQ ID NOS: 21

<210> SEQ ID NO 1
<211> LENGTH: 19
<212> TYPE: DNA
<213> ORGANISM: Homo sapiens

<400> SEQUENCE: 1
tagcgtgtga atcggacat                                         19

<210> SEQ ID NO 2
<211> LENGTH: 20
<212> TYPE: DNA
<213> ORGANISM: Homo sapiens

<400> SEQUENCE: 2
ttgactgggc agatagggga                                        20

<210> SEQ ID NO 3
<211> LENGTH: 20
<212> TYPE: DNA
<213> ORGANISM: Homo sapiens

<400> SEQUENCE: 3

```
atagttcacc catggaaacc                                              20

<210> SEQ ID NO 4
<211> LENGTH: 20
<212> TYPE: DNA
<213> ORGANISM: Homo sapiens

<400> SEQUENCE: 4
ggaggagaat cttagggaaa                                              20

<210> SEQ ID NO 5
<211> LENGTH: 16
<212> TYPE: DNA
<213> ORGANISM: Homo sapiens

<400> SEQUENCE: 5
actggactcc cgctgg                                                  16

<210> SEQ ID NO 6
<211> LENGTH: 19
<212> TYPE: DNA
<213> ORGANISM: Homo sapiens

<400> SEQUENCE: 6
cgctcagcct ccataaatc                                               19

<210> SEQ ID NO 7
<211> LENGTH: 25
<212> TYPE: DNA
<213> ORGANISM: Homo sapiens

<400> SEQUENCE: 7
caacttcatt tcttttcagt acctt                                        25

<210> SEQ ID NO 8
<211> LENGTH: 20
<212> TYPE: DNA
<213> ORGANISM: Homo sapiens

<400> SEQUENCE: 8
ctgtccagat accatttctc                                              20

<210> SEQ ID NO 9
<211> LENGTH: 22
<212> TYPE: DNA
<213> ORGANISM: Homo sapiens

<400> SEQUENCE: 9
agcatccatc tcttgaagac at                                           22

<210> SEQ ID NO 10
<211> LENGTH: 23
<212> TYPE: DNA
<213> ORGANISM: Homo sapiens

<400> SEQUENCE: 10
gcatgtttct gccaataatc tct                                          23

<210> SEQ ID NO 11
<211> LENGTH: 17
<212> TYPE: DNA
<213> ORGANISM: Homo sapiens
```

```
<400> SEQUENCE: 11
caacttcagc aggctgt                                                      17

<210> SEQ ID NO 12
<211> LENGTH: 21
<212> TYPE: DNA
<213> ORGANISM: Homo sapiens

<400> SEQUENCE: 12
agtctgagaa gcatcaattt t                                                 21

<210> SEQ ID NO 13
<211> LENGTH: 24
<212> TYPE: DNA
<213> ORGANISM: Homo sapiens

<400> SEQUENCE: 13
cattttctaa atgcctccct taaa                                              24

<210> SEQ ID NO 14
<211> LENGTH: 19
<212> TYPE: DNA
<213> ORGANISM: Homo sapiens

<400> SEQUENCE: 14
gtccattagg cacaaaaag                                                    19

<210> SEQ ID NO 15
<211> LENGTH: 34
<212> TYPE: DNA
<213> ORGANISM: Artificial Sequence
<220> FEATURE:
<223> OTHER INFORMATION: Synthetic DNA

<400> SEQUENCE: 15
cgcacgacat ggaaaaaaaa aatccgtgcg taaa                                   34

<210> SEQ ID NO 16
<211> LENGTH: 33
<212> TYPE: DNA
<213> ORGANISM: Artificial Sequence
<220> FEATURE:
<223> OTHER INFORMATION: Synthetic sequence

<400> SEQUENCE: 16
cgtcgaacct taaaaaaaaa agttaccgac gaa                                    33

<210> SEQ ID NO 17
<211> LENGTH: 36
<212> TYPE: DNA
<213> ORGANISM: Artificial Sequence
<220> FEATURE:
<223> OTHER INFORMATION: synthetic DNA

<400> SEQUENCE: 17
cgcacgactt attaaaaaaa aatgacagtg cgtaaa                                 36

<210> SEQ ID NO 18
<211> LENGTH: 33
<212> TYPE: DNA
<213> ORGANISM: Artificial Sequence
<220> FEATURE:
<223> OTHER INFORMATION: synthetic DNA

<400> SEQUENCE: 18
```

```
cgtcggtacc ttaaaaaaaa acatcacgac gaa                          33

<210> SEQ ID NO 19
<211> LENGTH: 23
<212> TYPE: DNA
<213> ORGANISM: Artificial Sequence
<220> FEATURE:
<223> OTHER INFORMATION: synthetic DNA

<400> SEQUENCE: 19
gtgcataaaa aaagagcact aaa                                     23

<210> SEQ ID NO 20
<211> LENGTH: 33
<212> TYPE: DNA
<213> ORGANISM: Artificial Sequence
<220> FEATURE:
<223> OTHER INFORMATION: synthetic DNA

<400> SEQUENCE: 20
cgcacttgcc aaaaaaaatt gatggtgcgt aaa                          33

<210> SEQ ID NO 21
<211> LENGTH: 30
<212> TYPE: DNA
<213> ORGANISM: Artificial Sequence
<220> FEATURE:
<223> OTHER INFORMATION: synthetic DNA

<400> SEQUENCE: 21 cgtcgcccttt aaaaaaaaac tgccgacgaa                             30
```